United States Patent [19]

Tatsuoka et al.

[11] Patent Number: 5,288,752
[45] Date of Patent: Feb. 22, 1994

[54] COMPOUND EFFECTIVE AS CEREBRAL INSUFFICIENCY IMPROVER

[75] Inventors: Toshio Tatsuoka, Nishinomiya; Kenji Suzuki, Osaka; Fumio Satoh, Nagaokakyo; Seiji Miyano, Fukuoka; Kunihiro Sumoto, Oonojo, all of Japan

[73] Assignee: Suntory Limited, Osaka, Japan

[21] Appl. No.: 980,238

[22] Filed: Nov. 23, 1992

Related U.S. Application Data

[62] Division of Ser. No. 737,717, Jul. 30, 1991, Pat. No. 5,179,092, which is a division of Ser. No. 286,857, Dec. 20, 1988, Pat. No. 5,057,514.

[30] Foreign Application Priority Data

| Dec. 22, 1987 | [JP] | Japan | 62-322951 |
| Feb. 3, 1988 | [JP] | Japan | 63-21863 |
| Sep. 5, 1988 | [JP] | Japan | 63-220497 |

[51] Int. Cl.⁵ ............................................. A61K 31/21
[52] U.S. Cl. .................................. 514/510; 552/307; 552/309; 552/310; 514/681
[58] Field of Search ............... 552/307, 309, 310; 514/681, 510

[56] References Cited

U.S. PATENT DOCUMENTS

| 4,774,241 | 9/1988 | Tatsuoka et al. | 514/227.5 |
| 5,057,514 | 10/1991 | Tatsuoka et al. | 514/227.5 |

OTHER PUBLICATIONS

The Merck Manual, pp. 1336–1340 (1987).
Wauqier, et al. "A New Antihypoxic Drug with Anti-convulsant Properties and Possible Effects on Cognitive Functions," *Drug Dev. Res.*, vol. 8, pp. 373–380 (1986).
Hackinski, et al., "Changing Concepts of Vascular Dementia" *Cerebrovascular Diseases*, Chapters 20–23, pp. 181–222 (1989).

*Primary Examiner*—Marianne M. Cintins
*Assistant Examiner*—Kimberly J. Kestler
*Attorney, Agent, or Firm*—Burns, Doane, Swecker & Mathis

[57] ABSTRACT

A compound having the formula (I):

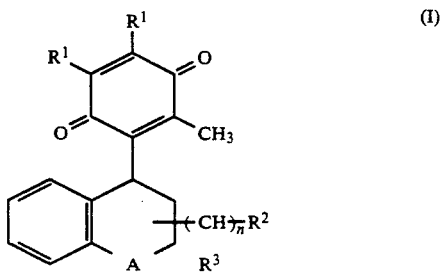

wherein A is —$CH_2$—, $R^1$ is $CH_3$ or $OCH_3$; $R^2$ is hydroxy or carboxy, carboxylic acid or carboxylic acid ester group; $R^3$ is H or a lower alkyl; and n is 0 or an integer of 1 to 6 or a pharmaceutically acceptable salt thereof.

10 Claims, No Drawings

COMPOUND EFFECTIVE AS CEREBRAL INSUFFICIENCY IMPROVER

This application is a continuation of application Ser. No. 07/737,717, filed Jul. 30, 1991 now U.S. Pat. No. 5,179,092 which is a divisional of application Ser. No. 07/286,857, filed Dec. 20, 1988 now U.S. Pat. No. 5,057,514.

BACKGROUND OF THE INVENTION

1. Field of the Invention

The present invention relates to novel compounds having the formula (I):

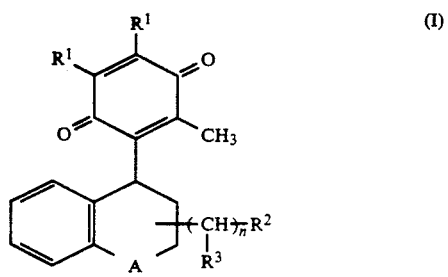

wherein A is $-CH_2-$, $-O-$, or $-S-$; $R^1$ is $CH_3$ or $OCH_3$; $R^2$ is hydroxy or carboxy which may be optionally esterized or amidated; $R^3$ is H or a lower alkyl; and n is 0 or an integer of 1 to 6, and an improver for cerebral insufficiency caused by cerebral ischemia containing the same.

The above-mentioned compounds (I) are effective for ameliorating and curing (or treating) various symptoms based on cerebral organic disorders as an oral medicine.

The term "cerebral organic disorders" used herein means various symptoms derived from cerebral ischemic diseases such as cerebral infarct sequela, cerebral hemorrhage sequela, and cerebral arteriosclerosis sequela and various organic disorders derived from senile dementia, dementia presenilis, amnesia, cephalic traumatic sequela, and cerebral operation sequela.

2. Description of the Related Art

The average human life-time has become prolonged, and the percentage of old people in the population is increasing. Accompanying this increase, senile dementia such as memorial dementia characterized by a loss of the memory function as a primary symptom is becoming a serious social problem.

At present, a large number of therapeutic drugs for senile dementia have been developed, but a satisfactory drug has not been developed yet.

The brain is an organ in which energy metabolism is most active, and if a disorder in the oxygen supply mechanism within the brain occurs, and an oxygen deficiency state (cerebral hypoxia) continues in the brain cells, a state will be finally reached in which no oxygen is supplied (cerebral anoxia). If such a state continues, the brain cells will be irreversibly damaged and will no longer be able to perform their normal functions.

At present, in the therapy of oxygen deficiency diseases accompanied by cerebral hypoxia or anoxia, a hypnolic such as phenobarbital has been employed, but the use thereof is limited because of the accompanying side effects on respiratory organs or the circulatory system.

SUMMARY OF THE INVENTION

An object of the present invention is to provide a novel compound having effective activities for a therapy of diseases caused by cerebral hypoxia or anoxia, by oral administration, and at low dose and low toxicity.

Other objects and advantages of the present invention will be apparent from the following description.

In accordance with the present invention, there is provided a novel compound having the formula (I):

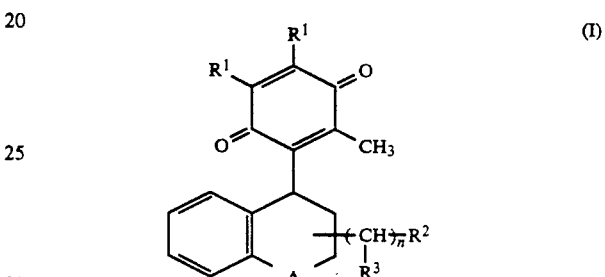

wherein A is $-CH_2-$, $-O-$, or $-S-$; $R^1$ is $CH_3$ or $OCH_3$; $R^2$ is hydroxy or carboxy which may be optionally esterized or amidated; $R^3$ is H or a lower alkyl; and n is 0 or an integer of 1 to 6, preferably 0 or an integer of 1 to 3. It should be noted that, although these compounds have the stereoisomers and optical isomers, these isomers are also included within the scope of the present invention.

In accordance with the present invention, there is also provided a cerebral insufficiency improver comprising, as an essential component, a compound having the above-mentioned formula (I) or a pharmaceutically acceptable salt thereof in a conventional pharmaceutically acceptable carrier.

DESCRIPTION OF THE PREFERRED EMBODIMENTS

The present inventors have found that the above-mentioned compounds (I) are very effective for a therapy of the above-mentioned diseases as a oral medicine at a low dose and with a low toxicity.

The compounds (I) according to the present invention can be prepared, for example, as follows.

The compounds (I-1) having a methylene group as a substituent A in the formula (I) can be prepared from the compounds of the compounds of the formulae (iii), (iv), (vi), and (ix), which can be prepared according to, for example, the following Routes A and B.

Route A

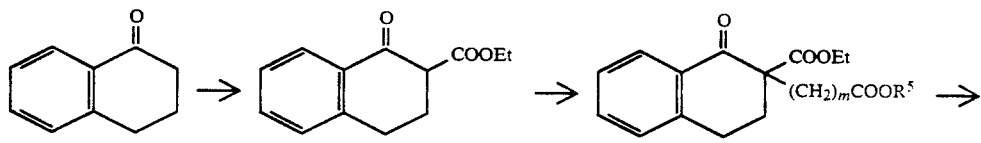

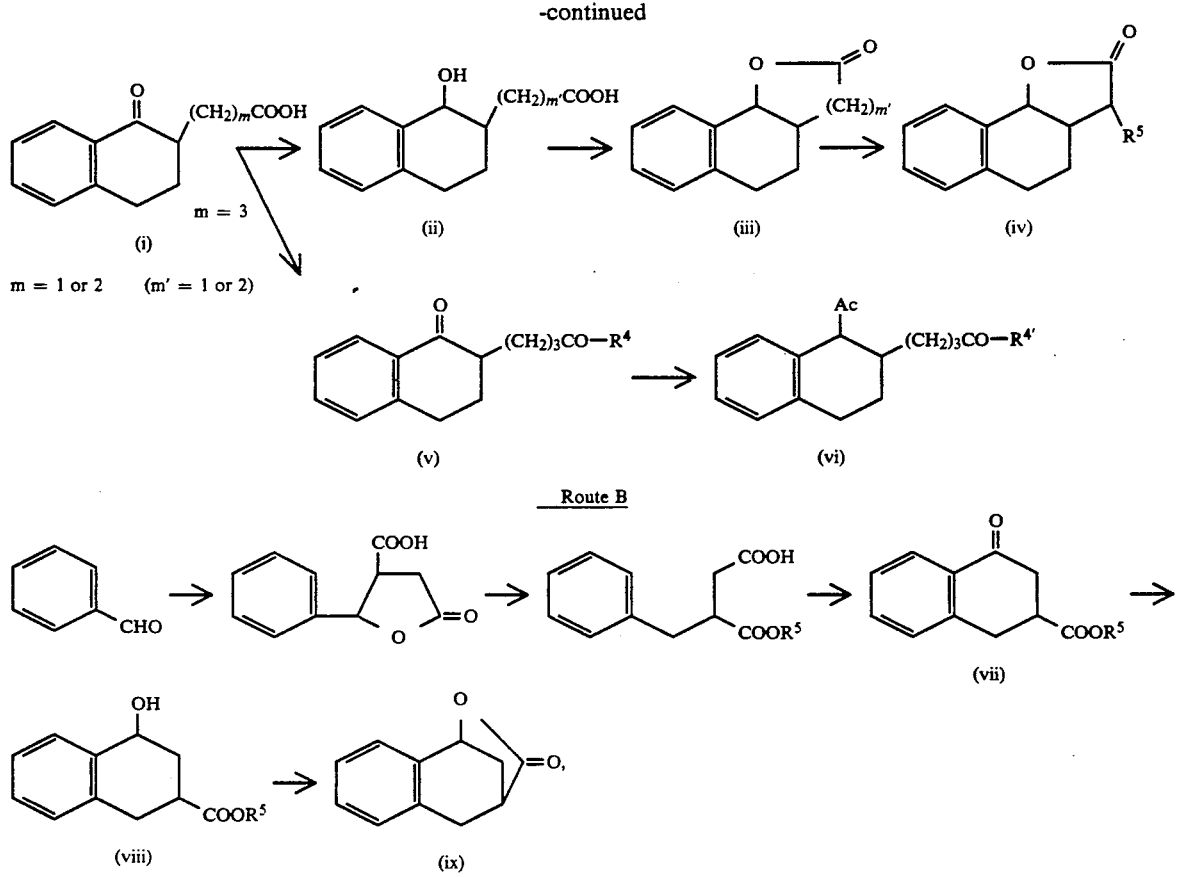

m = 1 or 2    (m' = 1 or 2)

Route B

(vii)

(viii)    (ix)

wherein m is an integer of 1 to 3; $R^{4'}$ is morpholino group, thiomorpholino group, piperidino group or N-methylpiperazinyl group; $R^5$ is a lower alkyl.

Namely, according to Route A, by reacting α-tetralone with diethyl carbonate in the presence of a base (e.g., sodium hydroxide) at a temperature from room temperature to 100° C., ethyl 1,2,3,4-tetrahydro-1-oxo-2-naphthalenecarboxylate is obtained. By reacting this with ethyl acrylate or a compound represented by the formula (VII):

$$X{+}CH_2{\rightarrow_m}COOR^5 \qquad (VII)$$

wherein X is a halogen atom, $R^5$ is a lower alkyl group and m is the same as defined above in a solvent which does not participate in the reaction, for example, ether, tetrahydrofuran, ethanol, in the presence of a base such as sodium hydride or sodium ethylate at 0° C. to room temperature. Thus, 2-ethoxycarbonyl-1,2,3,4-tetrahydro-1-oxo-2-naphthalene alkylene carboxylic acid ester is obtained.

This compound is hydrolyzed while refluxing under heating for 1 to 20 hours in the presence of a base (e.g., sodium hydroxide, potassium hydroxide, and sodium carbonate) in a mixture of an organic solvent (e.g., dioxane, tetrahydrofuran, ethanol) and water. Thereafter, the pH of the reaction mixture is adjusted by using an acid such as concentrated hydrochloric acid to pH 1 to 2 to effect the decarboxylation reaction to obtain a compound represented by the formula (i) in the Route A.

The compounds obtained above having m=1 or 2 are reduced with sodium borohydride by adding a reducing agent, for example, sodium borohydride, to a solvent which does not participate in the reaction, such as, ethanol or methanol, at a temperature of from 0° C. to room temperature or catalytically reduced under hydrogen gas stream with the use of palladium-carbon as a catalyst in a solvent such as, for example, dioxane, ethanol, methanol or tetrahydrofuran, followed by post-treatment in a conventional manner, to obtain a compound represented by the formula (ii) having m'=1 or 2. The resultant compound can be lactonized in a solvent such as toluene or benzene, in the presence of a catalyst (e.g., hydrochloric acid, p-toluenesulfonic acid, D,L-camphorsulfonic acid) at room temperature to 150° C. or lactonized with the use of a dehydrating condensing agent (e.g., dicyclohexylcarbodiimide, ethyl chlorocarbonate-triethylamine, 1-ethyl-3-(3-dimethylaminopropyl)-carbodiimide hydrochloride) to obtain a compound represented by the formula (iii).

The compounds represented by the formula (iii) having m'=1 can be converted to a compound represented by the formula (iv) by reacting with an alkylating agent such as methyl iodide in the presence of lithium isopropylcyclohexylamide in a solvent which does not participate in the reaction such as tetrahydrofuran, benzene at a temperature of −78° C. to −30° C.

On the other hand, the compounds represented by the formula (i) having m=3 can be converted to the compound represented by the formula (v) by condensation with alcohols or amides, for example, morpholine or thiomorpholine, using 1-ethyl-3-(3-dimethylaminopropyl)carbodiimide hydrochloride in a solvent which does not participate in the reaction such as methylene chloride or benzene.

The resultant compound (v) is reacted in a solvent which does not participate in the reaction such as ethanol, methanol by adding reducing agent, for example, sodium borohydride at a temperature of 0° C. to room temperature, to obtain the hydroxy compound.

This product is acetylated with acetic anhydride in the presence of a base such as 4-dimethylamino pyridine, pyridine in a solvent which does not participate in the reaction, such as methylene chloride, to obtain the compound represented by the formula (vi).

According to Route B, a substituted benzaldehyde and succinic anhydride are subjected to condensation together with a Lewis acid such as zinc chloride and triethylamine in a solvent which does not participate in the reaction at, for example, a temperature of 0° to 50° C., preferably room temperature, to form a butyrolactone carboxylic acid derivative, which compound is esterified to be converted to a lower alkyl ester, followed by catalytic reduction in the presence of palladium black or palladium-carbon in an inert solvent such as dioxane, ethanol or tetrahydrofuran, whereby β-ethoxycarbonyl-γ-phenyl butyrate can be obtained. Next, this compound is subjected directly to ring closure by use of a polyphosphoric acid, or alternatively, the compound is converted to acid chloride by a conventional method and then subjected to an intramolecular Friedel-Crafts reaction in the presence of a Lewis acid catalyst such as aluminum chloride or boron trifluoride-ether complex, whereby a compound represented by the formula (vii) can be obtained. As in the above-mentioned Route A, the compound (vii) can be converted to the compound (viii), subsequently to the compound (ix).

The compound (iii), (iv) or (vi) obtained according to the Route A or the compound (ix) obtained according to the Route B is condensed with a hydroquinone derivative having the formula (VIII):

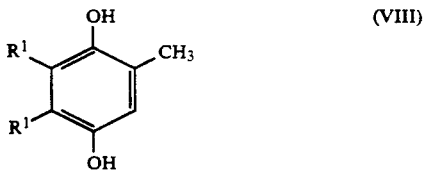

(VIII)

wherein $R^1$ is as defined above, and then immediately oxidized with an oxidizing agent such as an aqueous ferric chloride, manganese dioxide or ceric ammonium nitrate, and subsequently amidated, esterified or reduced by a conventional method, whereby the compound of the formula (I-1) having a methylene group as a substituent A in the formula (I) of the present invention can be obtained.

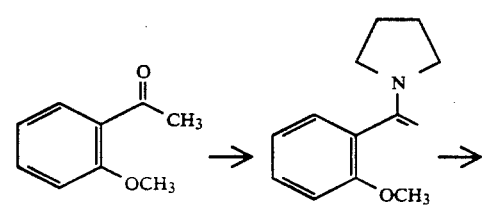

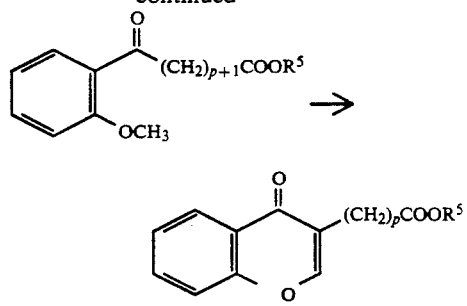

The compounds (I-2) in the present invention represented by the formula (I) having an oxygen atom as a substituent A can be prepared, for example, as follows:

Namely, by heating o-methoxyacetophenone and pyrrolidine under reflux in a solvent such as benzene, in the presence of p-toluene sulfonic acid, a compound having the formula:

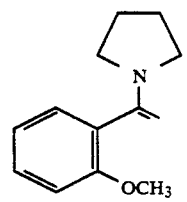

is obtained. This compound is reacted with ethylbromoacetate or ethyl acrylate in a solvent which does not participate in the reaction, such as benzene or dioxane, and then hydrolyzed in conventional manner, whereby o-methoxy benzoylalkylene carboxylic acid ester is obtained. This ester derivative is treated with a Lewis acid such as aluminum chloride in a solvent which does not participate in the reaction, such as 1,2-dichloroethane, to be readily converted to a demethylated derivative.

The demethylated derivative is heated in N,N-dimethylformamide (hereinafter abbreviated as DMF) at about 100° C. in the presence of a boron trifluoride-ether complex for 5 to 30 hours, and then methanesulfonyl chloride is added, followed by heating at about 100° C. for 3 to 10 hours, whereby 4-oxo-1-chromene-3-alkylenecarboxylic acid ester is obtained.

The above-mentioned ester can be converted to the corresponding hydroxyl compound, subsequently, lactone in the same manner as mentioned above and the compound represented by the general formula (x) can be obtained

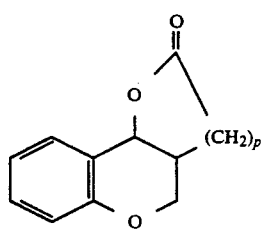

(x)

wherein p is as defined above.

On the other hand, a known compound. 4-oxo-4H-1-benzopyran-2-carboxylic acid is esterified according to a conventional manner, and then, reduced to the compound, 4-hydroxy-4H-2,3-dihydro-1-benzopyran-2-carboxylic acid ester.

The resultant ester is converted to the corresponding lactone is the same manner as mentioned above to obtain the compound represented by the formula (xi).

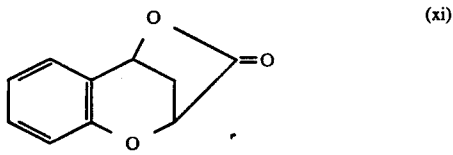

can be obtained.

The resultant compound (x) or (xi) is condensed with a hydroquinone derivative represented by the formula (VIII) and, in the same manner as mentioned above, the compound of the present invention represented by the formula (I-2) having an oxygen atom as a substituent A in the formula (I) can be obtained.

Furthermore, the compound of the present invention represented by the formula (I-3) having a sulfur atom as a substituent A in the formula (I) can be prepared, for example, as follows.

Namely, a known compound, 4-oxo-1-thiocoumarone-3-methyl carboxylic acid (see JP-A-62-252789) is converted, in the same manner as mentioned above, to the corresponding hydroxy compound, subsequently lactone. Thus, the compound having the formula (xii) can be obtained.

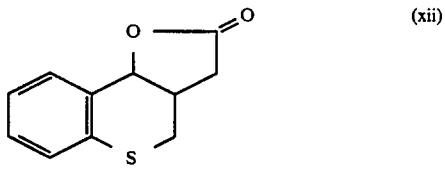

The resultant compound (xii) is condensed with the hydroquinone derivative having the formula (VIII) and, in the same manner as mentioned above, the compound of the present invention represented by the formula (I-3) having a sulfur atom as a substituent A in the formula (I) is obtained.

The compounds having the general formula (I) according to the present invention can be orally administered alone or in combination with pharmaceutically acceptable conventional carriers and fillers in a variety of dosage forms such as tablets, troches, pills, granules, powders, capsules, and the like. The carriers include, for example, starch, dextrin, sucrose, lactose, silic acid, carboxymethylcellulose, cellulose, gelatin, polyvinylpyrrolidone, glycerin, agar, calcium carbonate, sodium bicarbonate, paraffin, cetyl alcohol, stearic acid esters, kaolin, bentonite, talc, calcium stearate, magnesium stearate, polyethyleneglycol, water, ethanol, isopropyl alcohol, and propyleneglycol and the like.

Although there are no critical limitations to the content of the compound (I) in the pharmaceutical preparation, the optimum content is 1% to 90% by weight, more preferably 5% to 50% by weight.

Although there are no critical limitations to the dosage of the present cerebral insufficiency improver, the optimum dosage of the compound (I) of the present invention is 0.1–1000 mg, preferably 10 to 500 mg, per day. This dosage can be suitably changed depending upon, for example, the characteristics of the subjects, including age, response, weight, severity of disease and the like, the dosage form, and the dosing frequency.

EXAMPLES

The present invention now will be further illustrated by, but is by no means limited to, the following Synthesis Examples, and Evaluation Examples.

REFERENCE EXAMPLE 1

Synthesis of 1,2,3,4-tetrahydro-1-oxo-2-naphthaleneacetic acid (Compound No. R-1)

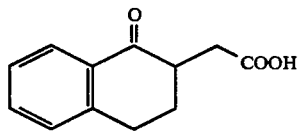

A suspension of 10 g (0.0684 mole) of α-tetralone, 3.56 g (0.0890 mole) of 60% sodium hydride and 32 g (0.2709 mole) of diethyl carbonate was heated under reflux for 1 hour, then poured into water, adjusted with conc. hydrochloric acid to a pH of 1 to 2, and extracted with ether. The ether layer was washed with water and then dried over magnesium sulfate. After evaporation of the solvent, the crude product was purified by silica gel column chromatography (hexane/ethyl acetate=9/1) to obtain 8.6 g of ethyl 1,2,3,4-tetrahydro-1-oxo-2-naphthalenecarboxylate, which was dissolved in tetrahydrofuran (220 ml) and then 1.90 g (0.0475 mole) of 60% sodium hydroxide was added under ice-cooling. After stirring for 30 minutes, 10.0 g (0.0599 mole) of ethyl bromoacetate was added, followed by stirring for 3 hours at room temperature. The reaction mixture was poured into ice-water, extracted with ether, and then the extract was subjected to washing with water, drying and solvent evaporation in a conventional manner. The crude product obtained was purified by silica gel column chromatography (hexane/ethyl acetate=5/1) to obtain 9.03 g of the following ethyl 2-ethoxycarbonyl-1,2,3,4-tetrahydro-1-oxo-2-naphthaleneacetate

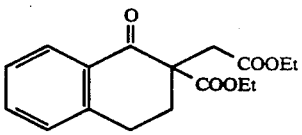

Then, this compound was heated under reflux in an aqueous 2N sodium hydroxide solution (100 ml) and dioxane (50 ml) for 8 hours. The reaction mixture was diluted with water, then adjusted to a pH of 1 to 2 with conc. hydrochloric acid, and extracted with ether. After subjecting the extract to washing with water, drying and solvent evaporation in a conventional manner, 5.4 g of the title compound was obtained.

REFERENCE EXAMPLE 2

Synthesis of
1,2,3,4-tetrahydro-1-oxo-2-naphthalenepropionic acid
(Compound No. R-2)

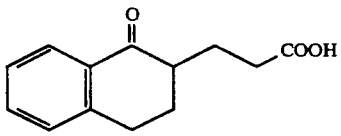

5.0 g (0.0229 mole) of ethyl 1,2,3,4-tetrahydro-1-oxo-2-naphthalenecarboxylate obtained in Reference Example 1 was added into an ethanolic (300 ml) solution of sodium ethoxide prepared from 158 mg (6.8695 mmole) of sodium, and then 2.99 g (0.0299 mole) of ethyl acrylate was added, followed by stirring at room temperature for 4 hours.

The reaction mixture was concentrated under a reduced pressure, diluted with water, and then extracted with ether. The extract was subjected to washing with water, drying and solvent evaporation in a conventional manner to obtain 5.6 g of ethyl 2-ethoxycarbonyl-1,2,3,4-tetrahydro-1-oxo-2-naphthalenepropionate.

This compound was heated under reflux in an aqueous 2N sodium hydroxide solution (200 ml) and dioxane (100 ml) for 8 hours. The reaction mixture was diluted with water, then adjusted to a pH of 1 to 2 with conc. hydrochloric acid and extracted with ether. After subjecting the extract to washing with water, drying and solvent evaporation in a conventional manner, 3.71 g of the title compound was obtained.

REFERENCE EXAMPLE 3

Synthesis of
1,2,3,4-tetrahydro-1-oxo-2-naphthalenebutyric acid
(Compound No. R-3)

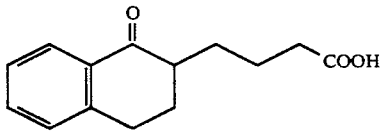

10.0 g (45.8715 mmole) of ethyl 1,2,3,4-tetrahydro-1-oxo-2-naphthalenecarboxylate obtained in Reference Example 1 was dissolved in 50 ml of 1,2-dimethoxyethane and the solution was added to the suspension of 2.3 g of 60% sodium hydride in 250 ml of 1,2-dimethoxyethane under ice-cooling.

Then, 14.4 g (71.773 mmole) of ethyl 4-bromobutyrate was added to the above solution. After the mixture was refluxed for 6 hours, the reaction mixture was poured in ice-water, followed by extracting with ether. The extracted solution was washed with water and dried in a conventional manner. After evaporation of the solvent, the crude product was purified by silica gel column chromatography (hexane/ethyl acetate=4/1) to obtain 6.86 g of ethyl 2-ethoxycarbonyl-1,2,3,4-tetrahydro-1-oxo-2-naphthalene-butyrate, which was dissolved in a mixture of 2N aqueous sodium hydroxide solution (160 ml) and dioxane (40 ml), followed by heating under reflux with stirring for 16 hours.

The reaction mixture was diluted with water and, after adjusting the pH to 1 to 2 with conc. hydrochloric acid, was extracted with ether. The extracted solution was washed with water, dried, and concentrated in a conventional manner to obtain 3.98 g of the title compound.

REFERENCE EXAMPLE 4

Synthesis of ethyl
1,2,3,4-tetrahydro-4-oxo-2-naphthoate (Compound No. R-4)

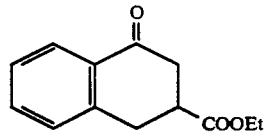

To a suspension of 10.6 g (0.1000 mole) of benzaldehyde, 15.0 g (0.1500 mole) of succinic anhydride and 30.0 g (0.2206 mole) of zinc chloride in methylene chloride (120 ml) was added, and then, after addition of 20.2 g (0.2000 mole) of triethylamine, and the mixture was stirred at room temperature for 16 hours.

To the reaction mixture 2N aqueous hydrochloric acid (500 ml) was added, and the mixture was extracted with ethyl acetate. The organic layer was washed with water, dried and then the solvent was evaporated. The crude product obtained was recrystallized from chloroform to obtain 13.13 g of β-carboxy-γ-phenyl-γ-butyrolactone as a mixture of cis-isomer and trans-isomer.

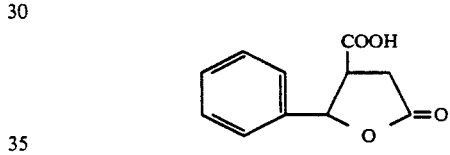

A methylene chloride solution (200 ml) of 3.25 g (15.758 mmole) of the compound obtained above (a mixture of cis- and trans-isomers), 867 mg (18.8478 mmole) of ethanol, 6.04 g (31.5075 mmole) of 1-ethyl-3-(3-dimetylaminopropyl) carbodiimide hydrochloride and 193 mg (1.5819 mmole) of 4-dimethylaminopyridine was stirred at room temperature for 8 hours.

The reaction mixture was washed with water, then dried and the solvent was evaporated. The crude product obtained was purified by silica gel column chromatography (hexane/ethyl acetate=3/1) to obtain 3.30 g of β-ethoxycarbonyl-γ-phenyl-γ-butyrolactone as a mixture of cis-isomer and trans-isomer.

A suspension of 1.0 g of palladium chloride in dioxane (40 ml) was stirred under a hydrogen gas stream at room temperature for 20 minutes. Next, a solution of 3.30 g of (14.1025 mmole) of the compound obtained above in dioxane (5 ml) was added and the mixture was stirred under a hydrogen gas stream at room temperature for 16 hours.

By filtering the reaction mixture and concentrating the filtrate under a reduced pressure, 3.32 g of β-ethoxycarbonyl-γ-phenylbutyric acid was obtained.

An amount of 1.30 g (5.5080 mmole) of the compound obtained above was added to oxalyl chloride (20 ml) and stirred at room temperature for 5 hours.

The reaction mixture was concentrated under a reduced pressure, the residue was dissolved in 1,2-dichloethane (70 ml), and 806 mg (6.0601 mmole) of aluminum chloride was added under ice-cooling, followed by stirring at room temperature for 16 hours. The reaction mixture was poured into 1N aqueous hydrochloric acid, and extracted with ether. The organic layer was washed with water, dried and then the solvent was evaporated. The crude product was purified by silica gel chromatography (hexane/ethyl acetate=2/1) to obtain 864 mg of the title compound.

REFERENCE EXAMPLE 5

Synthesis of ethyl 4-oxo-1-chromene-3-acetate (Compound No. R-5)

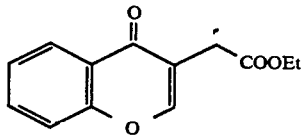

An amount of 15 g (0.1000 mole) of o-methoxyacetophenone, 7.8 g (0.1097 mole) of pyrrolidine and 100 mg (0.526 mmole) of p-toluenesulfonic acid monohydrate were dissolved in benzene, and the benzene solution (60 ml) was heated under reflux for 14 hours and superfluous solvent was evaporated by concentration under a reduced pressure. To the residue obtained, benzene (100 ml) and 25 g of ethylbromoacetate (0.1500 mole) were added, and the mixture was heated under reflux for 4 hours.

The reaction mixture was cooled, then concentrated under a reduced pressure and the residue obtained was dissolved in a mixture of methanol/water=100 ml/20 ml. The solution was heated under reflux for 2 hours, then methanol was evaporated under a reduced pressure, and thereafter, the reaction mixture was diluted with water and extracted with ether.

The extract layer obtained was washed with dil. hydrochloric acid, saturated aqueous sodium chloride and dried over anhydrous magnesium sulfate, followed by concentration under a reduced pressure.

The crude product obtained was purified by silica gel column chromatography (hexane/ethyl acetate=4/1) to obtain 8.3 g of ethyl o-methoxybenzoylpropionate.

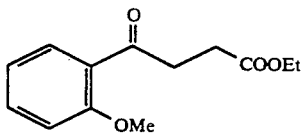

This compound was dissolved in methylene chloride and to the solution (250 ml), 16.5 g (0.124 mole) of aluminum chloride was added under ice-cooling. After stirring at room temperature for 5 hours, the reaction mixture was diluted with cold dil. hydrochloric acid, followed by extraction with chloroform.

The extract layer obtained was washed with water, then dried and the solvent was evaporated to obtain 6.8 g of ethyl o-hydroxybenzoylpropionate.

This compound was then dissolved in DMF (39 ml), and to the solution, 23 ml of boron trifluoride-diethyl ether was added under ice-cooling. After stirring at room temperature for 30 minutes, the mixture was further stirred at 100° C. for 14 hours. Next, to the reaction mixture was added 10.8 g (0.083 mole) of methanesulfonyl chloride, and after heating under reflux for 6 hours, the reaction mixture was diluted with ice-water and extracted with ether.

The extract layer obtained was washed with water, dried and the solvent was evaporated. The residue obtained was purified by silica gel column chromatography (hexane/ethyl acetate=2/1) to obtain 5.0 g of the title compound.

REFERENCE EXAMPLE 6

Synthesis of ethyl 4-oxo-1-chromene-3-propionate (Compound No. R-6)

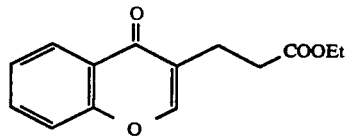

Similarly as in Reference Example 5, 10 g (0.067 mole) of o-methoxyacetophenone, 5.21 g (0.073 mole) of pyrrolidine, and 50 mg (0.263 mmole) of p-toluenesulfonic acid monohydrate were dissolved in benzene (60 ml), the benzene solution was heated under reflux for 16 hours, and superfluous solvent was evaporated by concentration under a reduced pressure. To the residue obtained were added 40 ml of dioxane and 10 g (0.100 mole) of ethyl acrylate, and the mixture was heated under reflux for 3 hours.

The reaction mixture was cooled, 10 ml of water was added and the mixture was heated under reflux for one hour, followed by concentration under a reduced pressure. The residue was diluted with ice-water, and then extracted with ether.

The extract layer obtained was washed with dil. hydrochloric acid and saturated aqueous sodium chloride, and then dried over anhydrous magnesium sulfate, followed by concentration under a reduced pressure.

The crude product obtained was purified by silica gel column chromatography (hexane/ethyl acetate=5/1) to obtain 6.3 g of ethyl o-methoxybenzoylbutyrate.

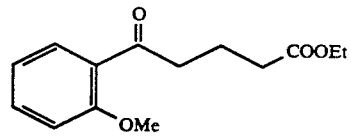

This compound was dissolved in 1,2-dichloroethane, and to the solution (250 ml), 10.07 g (0.076 mole) of aluminum chloride was added under ice-cooling, and the mixture was stirred at room temperature for 3 hours. Next, the reaction mixture was diluted with cold dil. hydrochloric acid and then extracted with chloroform.

The extract layer obtained was washed with water, then dried and the solvent was evaporated to obtain 5.41 g of ethyl o-hydroxybenzoylbutyrate.

This compound was dissolved in DMF (29 ml), to the solution was added 17 ml of boron trifluoride-diethyl ether under ice-cooling, and after stirring at room temperature for 30 minutes, the mixture was heated under reflux for 20 hours. Next, 7.9 g (69 mmole) of methanesulfonyl chloride was added to the reaction mixture, and after heating under reflux for 4 hours, the reaction mixture was diluted with ice-water and extracted with ether.

The extract layer obtained was washed with water, dried and then the solvent was evaporated. The residue was purified by silica gel column chromatography (hexane/ethyl acetate=2/1) to obtain 4.07 g of the title compound.

REFERENCE EXAMPLE 7

Synthesis of 2,3,3a,4,5,9b-hexahydronaphtho[1,2-b]-furan-2-one (Compound No. R-7)

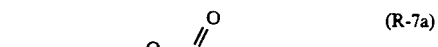

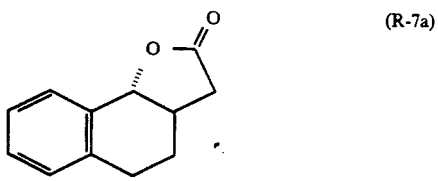

To an ethanol solution (100 ml) of 4.0 g (0.0196 mole) of the compound of Reference Example 1, 2.24 g (0.0589 mole) of sodium borohydride was added at 0° C., and the mixture was stirred at room temperature for 5 hours.

The reaction mixture was concentrated under a reduced pressure, then diluted with water, adjusted to a pH of 1 to 2 with conc. hydrochloric acid, and thereafter, extracted with ether. The extract was treated in a conventional manner, the crude product was then dissolved in methylene chloride (220 ml), and to the resultant solution was added 9.31 g (0.0486 mole) of 1-ethyl-3-(3-dimethylaminopropyl) carbodiimide hydrochloride, followed by stirring at room temperature for 3 hours.

The reaction mixture was washed with water, dried and the solvent was evaporated. The crude product obtained was purified by silica gel chromatography (hexane/ethyl acetate=5/2) to obtain two isomers (R-7a, R-7b) of the title compound in amounts of 1.91 g and 0.64 g, respectively.

REFERENCE EXAMPLE 8

Synthesis of 2,3,3a,4,5,9b-hexahydro-3-methylnaphtho[1,2-b]furan-2-one (Compound No. R-8)

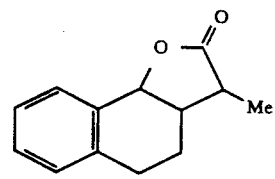

A solution of 1.0 g (5.319 mmole) of the compound of Reference Example 7 (R-7a) in THF (5 ml) was added, with stirring, to a THF solution (20 ml) of lithium isopropylcyclohexylamide, prepared from 750 mg (5.319 mmole) of isopropylcyclohexylamine and 3.39 ml of n-butyl lithium in hexane solution (1.57 mol/l) at a temperature of −78° C., followed by stirring at the same temperature for 30 minutes.

Next, a THF solution (5 ml) of 793 mg (5.5868 mmole) of methyl iodide was added thereto, followed by further stirring for 2 hours. After stirring, the reaction mixture was poured in water, followed by extracting with ether. The extracted layer was washed with a saturated sodium chloride solution, dried over magnesium sulfate. After evaporating the solvent, the crude product thus obtained was purified by silica gel chromatography (hexane/ethyl acetate=6/1) to obtain 430 mg of the title compound (R-8a).

Similarly, 483 mg of the title compound (R-8b) was obtained from 1.0 g of the compound R-7b.

REFERENCE EXAMPLE 9

Synthesis of 3,4,4a,5,6,10-hexahydro-2H-naphtho-[1,2-b]pyran-2-one (Compound No. R-9)

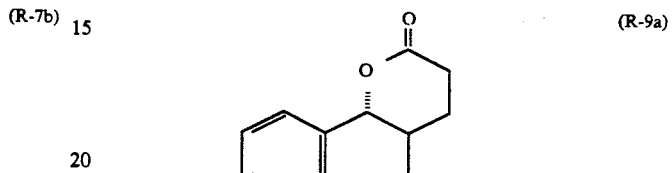

To an ethanol solution (80 ml) of 3.81 g (0.0175 mole) of the compound of Reference Example 2, 2.00 g (0.0526 mole) of sodium borohydride was added at 0° C., and the mixture was stirred for 5 hours.

The reaction mixture was concentrated under a reduced pressure, then diluted with water, adjusted to a pH of 1 to 2 with conc. hydrochloric acid, and thereafter, extracted with ether. The extract was treated in conventional manner, the crude product was then dissolved in methylene chloride (400 ml), and to the resultant solution, 7.93 g (0.0414 mole) of 1-ethyl-3-(3-dimethylaminopropyl)-carbodiimide hydrochloride was added, followed by stirring at room temperature for 3 hours.

The reaction mixture was washed with water, dried and the solvent was evaporated. The crude product obtained was purified by silica gel chromatography (hexane:ethyl acetate=5:2) to obtain two isomers (R-9a, R-9b) of the title compound in amounts of 1.33 g and 0.57 g, respectively.

REFERENCE EXAMPLE 10-(1)

Synthesis of 1-acetoxy-2-(4-thiomorpholino-4-oxobutyl)-1,2,3,4-tetrahydronaphthalene (Compound No. R-10-(1))

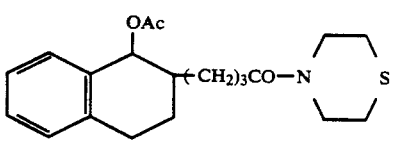

An amount of 620 mg (3.234 mmole) of 1-ethyl-3-(3-dimethylaminopropyl) carbodiimide hydrochloride was added to a methylene chloride solution (30 ml) of 499 mg (2.151 mmole) of the compound R-3 obtained in Reference Example 3 and 276 mg (2.680 mmole) of thiomorpholine, followed by stirring at room temperature for 3 hours.

The reaction mixture was washed with 1N hydrochloric acid and a saturated aqueous sodium chloride solution and dried. The solvent was distilled off to obtain 654 mg of 1-oxo-2-(4-thiomorpholino-4-oxobutyl)-1,2,3,4-tetrahydronaphthalene.

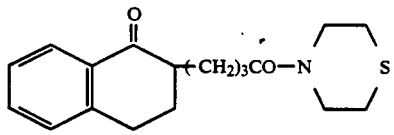

This compound was dissolved in an ethanol solution and sodium borohydride was added thereto under ice-cooling, followed by stirring at room temperature for 6 hours. Then, the reaction mixture was concentrated under a reduced pressure, diluted with dil. hydrochloric acid, and extracted with ether. The extracted layer was washed with water and the solvent was distilled off. The resultant residue was dissolved in methylene chloride and, to the solution, pyridine, acetic anhydride and dimethylamino pyridine were added, followed by stirring at room temperature for 16 hours.

The reaction mixture was washed with 1N hydrochloric acid and an aqueous saturated sodium chloride solution and dried, followed by concentrating under a reduced pressure.

The resultant crude product was purified by silica gel column chromatography (hexane/ethyl acetate=3/1) to obtain 600 mg of the title compound.

REFERENCE EXAMPLE 10-(2)

Synthesis of 1-acetoxy-2-(4-morpholino-4-oxobutyl)-1,2,3,4-tetrahydronaphthalene (Compound No. R-10-(2))

1-Oxo-2-(4-morpholino-4-oxobutyl)-1,2,3,4-tetrahydronaphthalene was obtained according to Reference Example 10-(1) by using morpholine instead of thiomorpholine.

Thereafter, the resultant compound was similarly acetylated and was purified by silica gel column chromatography (hexane/ethyl acetate=5/3) to obtain the title compound.

REFERENCE EXAMPLE 10-(3)

Synthesis of 1-acetoxy-2-(4-piperidino-4-oxobutyl)-1,2,3,4-tetrahydronaphthalene (Compound No. R-10-(3))

1-Oxo-2-(4-pyperidino-4-oxobutyl)-1,2,3,4-tetrahydronaphthalene was obtained, according to Reference Example 10-(1), by using piperidine instead of thiomorpholine.

Thereafter, the resultant compound was similarly acetylated and was purified by silica gel column chromatography (methylene chloride/acetone=50/1) to obtain the title compound.

REFERENCE EXAMPLE 11

Synthesis of 2,3-benzo-6-oxo-7-oxabicyclo[3,2,1]-octane (Compound No. R-11)

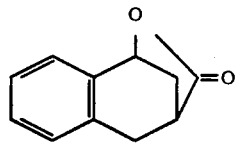

To a solution of 2.88 g (13.2110 mmole) of the compound of Reference Example 4 in ethanol (80 ml), 1.51 g (39.7368 mmole) of sodium borohydride was added under ice-cooling, and the mixture was stirred for 4 hours.

The reaction mixture was concentrated under a reduced pressure, the residue was diluted with 2N aqueous hydrochloric acid and extracted with ether. The organic layer was washed with water, dried and concentrated under a reduced pressure to give 2.76 g of ethyl 1,2,3,4-tetrahydro-4-hydroxy-2-naphthoate as a mixture of cis-isomer (over 90%) and trans-isomer.

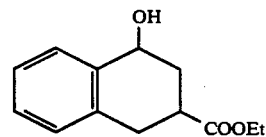

To a solution of the resultant compound in dioxane (50 ml), 3% aqueous potassium hydroxide (100 ml) was added and the mixture was stirred at room temperature for 8 hours.

The reaction mixture was diluted with water, adjusted to a pH of 1 to 2 with conc. hydrochloric acid, and extracted with ether. The extract obtained was washed with water, dried over magnesium sulfate, and further concentrated under a reduced pressure. The residue obtained was dissolved in methylene chloride (500 ml) and 5.03 g (26.227 mmole) of 1-ethyl-3-(3-dimethylaminopropyl)carbodiimide hydrochloride was added, followed by stirring at room temperature for 4 hours. The reaction mixture was washed with water, dried and then the solvent was evaporated. The crude product was purified by silica gel column chromatography (hexane:ethyl acetate=3:1) to obtain 971 mg of the title compound.

REFERENCE EXAMPLE 12

Synthesis of 2,3,3aα,9bβ-tetrahydro-2-oxofurano-[4,5-c]-1-chroman (Compound No. R-12a) and 2,3,3aα,9bα-tetrahydro-2-oxofurano-[4,5-c]-1-chroman (Compound No. R-12b)

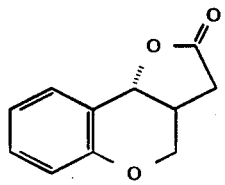

R-12a

-continued

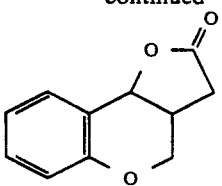
R-12b

An amount of 1.65 g (7.112 mmole) of the compound of Reference Example 5 was dissolved in ethanol, and the solution (100 ml) was stirred under a hydrogen gas stream in the presence of 800 mg of 5% palladium-carbon for 3 days.

Next, after the reaction mixture was filtered, the filtrate was concentrated under a reduced pressure and the residue obtained was subjected to silica gel column chromatography (hexane/ethyl acetate=2/1) for purification to obtain 1.43 g of ethyl 4-hydroxy-1-chroman-3-acetate as a mixture of the isomers.

This compound was dissolved in dioxane (5 ml), and to the solution was added 5% aqueous potassium hydroxide (20 ml), and the mixture was heated under reflux for 3 hours.

The reaction mixture was cooled, diluted with water, and the liquid property was made acidic (pH=1 to 2) by an addition of conc. hydrochloric acid, followed by ether extraction.

The ether layer obtained was washed with water, dried over magnesium sulfate, and the solvent was evaporated. The crude product obtained was dissolved in dichloromethane (300 ml), 2.79 g (14.554 mmole) of 1-ethyl-3-(3-dimethylaminopropyl)carbodiimide hydrochloride was added, and the mixture was stirred at room temperature for 3 hours.

The reaction mixture was washed with water, dried over magnesium sulfate and concentrated under a reduced pressure. The crude product obtained was purified by silica gel column chromatography (hexane/ethyl acetate=2/1) to obtain 590 mg of the title compound R-12a and 278 mg of R-12b.

REFERENCE EXAMPLE 13

Synthesis of 3,4,4aα,10bβ-tetrahydro-2-oxopyrano-[5,6-c]-1-chroman (Compound No. R-13a) and 3,4,4aα,10bα-tetrahydro-2-oxopyrano[5,6-c]-1-chroman (Compound No. R-13b)

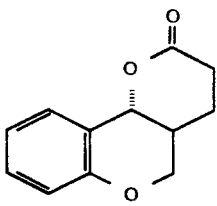
R-13a

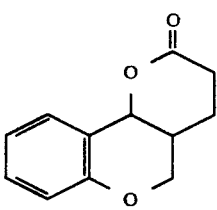
R-13b

An amount of 5.55 g (22.561 mmole) of the compound of Reference Example 6 was dissolved in etha-nol, and the solution (150 ml) was stirred under a hydrogen gas stream in the presence of 5% palladium-carbon (1000 mg) for 3 days.

Next, after the reaction mixture was filtered, the filtrate was concentrated under a reduced pressure, and the residue obtained was purified by silica gel column chromatography (hexane/ethyl acetate=3/1) to obtain ethyl 4-hydroxy-1-chroman-3-propionate as 1.59 g of trans isomer and 1.87 g of cis isomer.

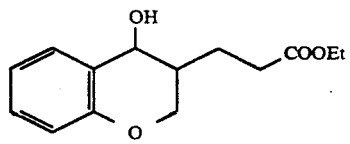

An amount of 1.59 g (6.360 mmole) of the resultant ethyl 4α-hydroxy-1-chroman-3β-propionate was dissolved in dioxane (15 ml), and to this solution, 5% aqueous potassium hydroxide (50 ml) was added and the mixture was heated under reflux for 2 hours.

The reaction mixture was cooled, diluted with water, and then the liquid property was made acidic (pH=1 to 2) by an addition of conc. hydrochloric acid, followed by ether extraction.

The extract layer obtained was washed water, dried over magnesium sulfate, and then concentrated under a reduced pressure. The residue obtained was dissolved in dichloromethane (500 ml), 3.58 g (18.675 mmole) of 1-ethyl-3-(3-dimethylaminopropyl)carbodiimide hydrochloride was added, and the mixture was stirred at room temperature for 4 hours.

The reaction mixture was washed with water, dried over magnesium sulfate, and then concentrated under a reduced pressure. The crude product obtained was purified by silica gel chromatography (hexane/ethyl acetate=2/1) to obtain 988 mg of the title compound R-13a.

Similarly, from ethyl 4α-hydroxy-a-chroman-3α-propionate, the title compound R-13b was obtained.

REFERENCE EXAMPLE 14

Synthesis of 3,4-benzo-7-oxo-2,6-dioxabicyclo-[3,2,1]octane (Compound No. R-14)

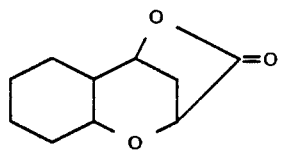

To an ethanol solution (200 ml) of 1.5 g (6.8807 mmole) of chromane-2-carboxylic acid, 200 mg of 5% palladium-carbon was added and the mixture was stirred at room temperature for 5 days.

The reaction mixture was filtered and the filtrate was concentrated under a reduced pressure. The resultant residue was purified by silica gel column chromatography (hexane/ethyl acetate=1/1) to obtain 520 mg of 2-ethoxycarbonyl-4-hydroxy-benzopyran.

To an ethanol solution (10 ml) of the compound obtained above, 20 ml of 3% aqueous potassium hydroxide was added, and the mixture was stirred at room temperature for one hour.

The reaction mixture was diluted with water, then washed with ether, and subsequently, the aqueous layer was adjusted to a pH of 1 to 2 with conc. hydrochloric acid, followed by extraction with ether. The ether layer was washed with water, dried, and then concentrated under a reduced pressure. Thereafter, the residue was suspended in methylene chloride (30 ml), 660 mg (3.4428 mmole) of 1-ethyl-3-(3-dimethylaminopropyl)-carbodiimide hydrochloride was added, and the mixture was stirred at room temperature for one hour. Subsequently, the reaction mixture was washed with water, dried, and then concentrated under a reduced pressure. The residue obtained was purified by silica gel column chromatography (hexane/ethyl acetate=2/1) to obtain 282 mg of the title compound.

REFERENCE EXAMPLE 15

Synthesis of 2,3,3aα,9bβ-tetrahydro-2-oxofurano-[4,5-c]-1-thiochroman (Compound No. R-15a) and 2,3,3aα,9bα-tetrahydro-2-oxofurano-[4,5-c]-1-thiochroman (Compound No. R-15b)

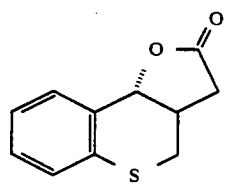
R-15a

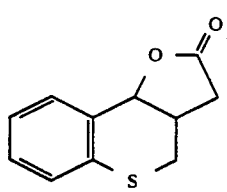
R-15b

To an ethanol solution (60 ml) of 1.47 g (6.622 mmole) of 4-oxo-1-thiochroman-3-acetic acid, 629 mg (16.553 mmole) of sodium borohydride was added at 0° C., and the mixture was stirred at the same temperature for 2 hours. The reaction mixture was concentrated under a reduced pressure, and the residue was diluted with water, adjusted to a pH of 1 to 2 with conc. hydrochloric acid and then extracted with ether. The extract layer was washed with water, dried over magnesium sulfate, and the solvent was evaporated. The crude product obtained was dissolved in methylene chloride (400 ml), then 3.17 g (16.536 mmole) of 1-ethyl-3-(3-dimethylaminopropyl)carbodiimide hydrochloride was added, and the mixture was stirred at room temperature for 4 hours. The reaction mixture was washed with water, dried, and the solvent was evaporated. The crude product obtained was purified by silica gel chromatography (hexane/ethyl acetate=3/1) to obtain 582 mg of the title compound R-15a and 420 mg of R-15b.

The physicochemical data of the compounds synthesized in the above Reference Examples 1 to 15 are shown in Table 1.

WORKING EXAMPLE 1

Synthesis of 1-(3,4-dimethoxy-6-methyl-2,5-benzoquinonyl)-1,2,3,4-tetrahydro-2-naphthaleneacetic acid (Compound No. 1)

To a 1,2-dichloroethane solution (20 ml) of 500 mg (2.6595 mmole) of the compound of Reference Example 7 (Compound No. R-7a) and 636 mg (3.4565 mmole) of 2,3-dimethoxy-5-methyl-1,4-hydroquinone, 566 mg (3.9878 mmole) of boron trifluoride-ether complex was added, and the mixture was stirred at room temperature for 16 hours. The reaction mixture was concentrated under a reduced pressure, then dissolved in a mixture of acetonitrile (15 ml) and water (5 ml) and 4.74 g (8.6496 mmole) of ceric ammonium nitrate (hereinafter called CAN) followed by stirring at room temperature for 30 minutes.

The reaction mixture was diluted with water, extracted with ether, and the extract was washed with water, and dried, followed by evaporation of the solvent. The crude product obtained was purified by silica gel chromatography (3%–5% methanol/dichloromethane) to obtain 620 mg of the title compound.

WORKING EXAMPLE 2

Synthesis of 1-(3,4-dimethoxy-6-methyl-2,5-benzoquinonyl)-1,2,3,4-tetrahydro-2-naphthalene-propionic acid (Compound No. 2)

To a 1,2-dichloroethane solution (20 ml) of 500 mg (2.4752 mmole) of the compound of Reference Example 9 (Compound No. R-9a) and 592 mg (3.2173 mmole) of 2,3-dimethoxy-5-methyl-1,4-hydroquinone, 526 mg (3.7060 mmole) of boron trifluoride-ether complex was added, and the mixture was stirred at room temperature for 16 hours. The reaction mixture was concentrated under a reduced pressure, dissolved in a mixed solution of acetonitrile (15 ml) and water (5 ml), and 3.4 g (6.2043 mmole) of CAN was added, followed by stirring at room temperature for 30 minutes. The reaction mixture was diluted with water, then extracted with ether, and the extract was washed with water, dried and the solvent was evaporated. The crude product was purified by silica gel chromatography (3–5% methanol/dichloromethane) to obtain 520 mg of the title compound.

WORKING EXAMPLE 3

Synthesis of 1-(3,4-dimethoxy-6-methyl-2,5-benzoquinonyl)-2-(2-thiomorpholino-2-oxoethyl)-1,2,3,4-tetrahydronaphthalene (Compound No. 3)

To a methylene chloride solution (20 ml) of 348 mg (0.9405 mmole) of the compound of Working Example 1 (Compound No. 1) and 145 mg (1.4077 mmole) of thiomorpholine 270 mg (1.4084 mmole) of 1-ethyl-3-(3-dimethylaminopropyl)-carbodiimide hydrochloride was added, and the mixture was stirred at room temperature for 6 hours.

The reaction mixture was washed with water, dried and the solvent was evaporated. The crude product obtained was purified by silica gel chromatography (hexane/ethyl acetate=1/1) to obtain 270 mg of the title compound.

WORKING EXAMPLE 4–10

Compound Nos. 4 to 10 were prepared from the compound Nos. 1 and 2 according to a method in Working Example 3.

WORKING EXAMPLE 11

Synthesis of 1-(3,4-dimethoxy-6-methyl-2,5-benzoquinonyl)-2-(4-thiomorpholino-4-oxobutyl)-1,2,3,4-tetrahydronaphthalene (Compound No. 11)

To a solution of 600 mg (1.662 mmole) of the compound R-10-(1) obtained in Reference Example 10 and 397 mg (2.158 mmole) of 2,3-dimethoxy-5-methyl-1,4-hydroquinone in 1,2-dichloroethane (8 ml), 80 μl of trifluoromethane sulfonic acid was added, followed by stirring at room temperature for 16 hours.

The reaction mixture was diluted with water followed by adding 0.4 g of manganese dioxide. After stirring at room temperature for 30 minutes, the mixture was subjected to ultrafiltration. The filtrate was concentrated under a reduced pressure. The crude product obtained was purified by silica gel chromatography (hexane/ethyl acetate=2/1) to obtain 238 mg of the title compound.

WORKING EXAMPLES 12 AND 13

Compound Nos. 12 and 13 were prepared according to a method in Working Example 11.

The structures of these compounds No. 1 to 13 are as follows.

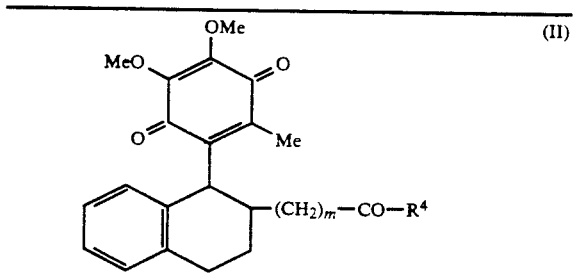

(II)

| Compound No. | m | R⁴ |
|---|---|---|
| 1 | 1 | OH |
| 2 | 2 | OH |
| 3 | 1 | N⌒S (thiomorpholino) |
| 4 | 1 | N⌒O (morpholino) |
| 5 | 1 | N⌒N—Me (N-methylpiperazino) |
| 6 | 1 | N (piperidino) |
| 7 | 1 | OEt |
| 8 | 2 | N⌒S (thiomorpholino) |
| 9 | 2 | N⌒O (morpholino) |
| 10 | 2 | OEt |
| 11 | 3 | N⌒S (thiomorpholino) |
| 12 | 3 | N⌒O (morpholino) |
| 13 | 3 | N (piperidino) |

WORKING EXAMPLE 14

Synthesis of 1,2,3,4-tetrahydro-4-(3,4-dimethoxy-6-methyl-2,5-benzoquinonyl)-2-naphtoic acid (Compound No. 14a, 14b)

To a solution of 654 mg (3.5543 mmole) of 2,3-dimethoxy-5-methyl-1,4-hydroquinone and 476 mg (2.7356 mmole) of the compound (R-11) of Reference Example 11 dissolved in 1,2-dichloroethane (20 ml), 582 mg (4.1006 mmole) of boron trifluoride-ether complex was added at room temperature, and the mixture was stirred for 16 hours.

The reaction mixture was concentrated under a reduced pressure, the residue was dissolved in a mixture of acetonitrile (15 ml) and water (5 ml), and 4.87 g (8.8868 mmole) of ceric ammonium nitrate was added, followed by stirring at room temperature for 30 minutes. The reaction mixture was poured into water and extracted with ether. The extract was washed with water, dried and then the solvent was evaporated. The residue obtained was purified and separated by silica gel column chromatography (5% methanol/dichloromethane) to obtain 120 mg of the stereoisomer 14a (cis-isomer), 83 mg of 14b (trans-isomer) and 450 mg of a mixture of 14a and 14b.

WORKING EXAMPLES 15–18

The following compounds 15–18 (i.e., cis-isomers 15a–18a and trans-isomers 15b–18b were prepared from Compound No. 14 according to the method of Working Example 3.

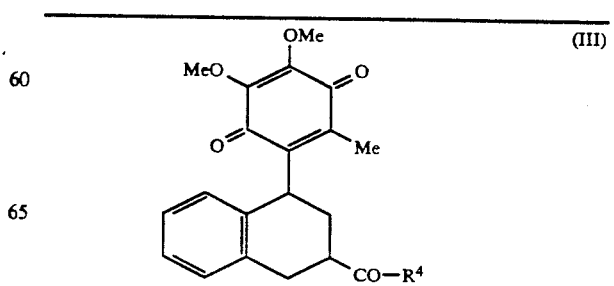

(III)

-continued

| Compound No. | R⁴ |
|---|---|
| 14 | OH |
| 15 |  |
| 16 |  |
| 17 | 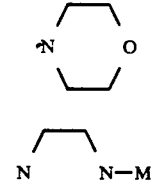 |
| 18 | 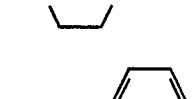 |

WORKING EXAMPLE 19

Synthesis of
(±)-4β-(3,4-dimethoxy-6-methyl-2,5-benzoquinonyl)-1-chroman-3α-acetic acid (Compound No. 19)

To a solution of 750 mg (3.947 mmole) of the compound (R-12b) of Reference Example 12 and 872 mg (4.739 mmole) of 2,3-dimethoxy-5-methyl-1,4-hydroquinone dissolved in 1,2-dichloroethane, 728 mg (5.129 mmole) of boron trifluoride-ether complex was added, and the mixture was stirred at room temperature for 15 hours. Subsequently, the reaction mixture was concentrated under a reduced pressure and the residue was dissolved in tetrahydrofuran (30 ml). Into the solution, 10% aqueous ferric chloride (30 ml) was added and the mixture was stirred at room temperature for 30 minutes. After stirring, the reaction mixture was diluted with water, and extracted with ether. The extract layer was washed with water, dried over magnesium sulfate, and the solvent was evaporated. The crude product obtained was subjected to silica gel column chromatography (5% methanol/methylene chloride) for purification to obtain 800 mg of the title compound.

Similarly, from 350 mg of R-12a, 258 mg of the title compound was obtained.

WORKING EXAMPLE 20

Synthesis of
(±)-4β-(3,4-dimethoxy-6-methyl-2,5-benzoquinonyl)-1-chroman-3α-propionic acid (Compound No. 20)

To a solution of 800 mg (3.922 mmole) of the compound (R-13b) of Reference Example 13 and 794 mg (4.315 mmole) of 2,3-dimethoxy-5-methyl-1,4-hydroquinone dissolved in 1,2-dichloroethane, 835 mg (5.883 mmole) of boron trifluoride-ether complex was added, and the mixture was stirred at room temperature for 20 hours. Next, the reaction mixture was concentrated under a reduced pressure, the residue obtained was dissolved in methylene chloride and 1.5 g of manganese dioxide was added, followed by stirring for 3 hours. The reaction mixture was filtered, and the filtrate was concentrated under a reduced pressure. The residue obtained was subjected to silica gel column chromatography (5% methanol/methylene chloride) for purification to obtain 310 mg of the title compound.

WORKING EXAMPLES 21-25

The following compounds 21 to 25 were prepared from the compound 19 and 20 according to a method of Working Example 3.

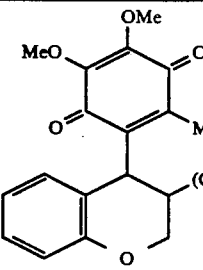 (IV)

| Compound No. | p | R⁴ |
|---|---|---|
| 19 | 1 | OH |
| 20 | 2 | OH |
| 21 | 1 | 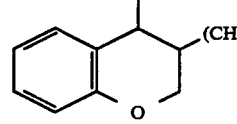 |
| 22 | 1 | 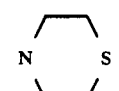 |
| 23 | 1 | 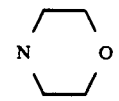 |
| 24 | 2 | 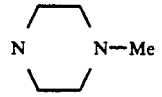 |
| 25 | 2 |  |

WORKING EXAMPLE 26

Synthesis of
2-carboxy-4-(3,4-dimethoxy-6-methyl-2,5-benzoquinonyl)-chroman (Compound No. 26)

To a 1,2-dichloroethane solution (40 ml) of 870 mg (4.7282 mmole) of 2,3-dimethoxy-5-methyl-1,4-hydroquinone, 610 mg (4.2978 mmole) of boron trifluoride ether complex was added, and after the mixture was stirred for 15 minutes, 756 mg (4.2954 mmole) of the compound (R-14) of Reference Example 14 was added, followed by stirring at room temperature for 16 hours.

Then, after the reaction mixture was concentrated under a reduced pressure, the residue was dissolved in tetrahydrofuran (30 ml), 10% aqueous ferric chloride (30 ml) was added, and the mixture was stirred at room temperature for one hour. The reaction mixture was concentrated under a reduced pressure, excessive tetrahydrofuran evaporated, and then the reaction mixture was diluted with water, followed by extraction with ether. The ether layer was washed with water, dried, then concentrated under a reduced pressure, and the residue was purified by silica gel column chromatography (5% methanol/dichloromethane) to obtain 520 mg of the title compound.

WORKING EXAMPLE 27-28

The following compounds 27 and 28 were prepared from the compound 26 according to a method of Example 3.

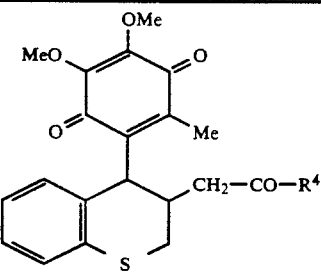

| Compound No. | R⁴ |
|---|---|
| 29 | OH |
| 30 | /‾‾\ N    S \__/ |
| 31 | /‾‾\ N    O \__/ |
| 32 | /‾‾\ N    N—Me \__/ |

| Compound No. | R⁴ |
|---|---|
| 26 | OH |
| 27 | /‾‾\ N    S \__/ |
| 28 | /‾‾\ N    O \__/ |

WORKING EXAMPLE 29

Synthesis of (±)-4β-(3,4-dimethoxy-6-methyl-2,5-benzoquinonyl)-1-thiochroman-3α-acetic acid (Compound No. 29)

To a solution of 500 mg (2.427 mmole) of the compound R-15a of Reference Example 15 and 447 mg (2.429 mmole) of 2,3-dimethoxy-5-methyl-1,4-dihydroquinone dissolved in 1,2-dichloroethane (40 ml), 448 mg (3.159 mmole) of boron trifluoride-ether complex was added, and the mixture was stirred at room temperature for 16 hours. The reaction mixture was concentrated under a reduced pressure, and then dissolved in methylene chloride (60 ml), followed by an addition of 1.06 g (12.192 mmole) of manganese dioxide and stirring at room temperature for 6 hours. The reaction mixture was filtered, and the crude product obtained by concentration of the filtrate under a reduced pressure was subjected to silica gel column chromatography (5% methanol/methylene chloride) for purification to obtain 340 mg of the title compound.

Although R-15b was used instead of R-15a, the title compound was still obtained.

WORKING EXAMPLES 30-32

The following compounds were prepared from the compound 29 according to a method of Working Example 3.

WORKING EXAMPLE 33

Synthesis of 1-(3,4-dimethoxy-6-methyl-2,5-benzoquinonyl)-1,2,3,4-tetrahydro-2-naphthaleneisopropionic acid (Compound No. 33)

To a 1,2-dichloroethane solution (20 ml) of 400 mg (1.9801 mmole) of the compound of Reference Example 8 (Compound No. R-8a) and 364 mg (1.9782 mmole) of 2,3-dimethoxy-5-methyl-1,4-hydroquinone, 365 mg (2.5716 mmole) of boron trifluoride-ether complex was added, and the mixture was stirred at room temperature for 12 hours. The reaction mixture was concentrated under a reduced pressure, then dissolved in a mixture of acetonitrile (15 ml)—water (5 ml) and 2.71 g (4.9452 mmole) of CAN was added, followed by stirring at room temperature for 20 minutes. The reaction mixture was diluted with water, then extracted with ether, and the extract was washed with water, dried and the solvent was evaporated. The crude product was purified by silica gel chromatography (5% methanol-methylene chloride) to obtain 364 mg of the title compound (33-a).

Similarly, 372 mg of the title compound (33-b) was obtained from 400 mg of the compound R-8b.

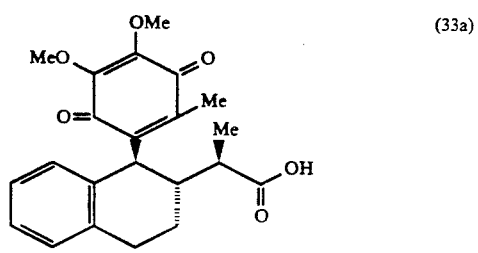

(33a)

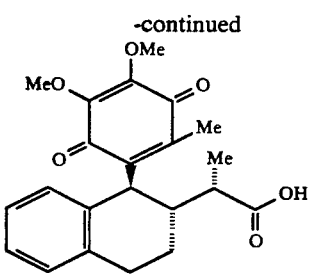
(33b)

WORKING EXAMPLES 34–35

The following compounds 34, 35, 34a, 34b, 35a, and 35b were prepared from the compound 33 according to a method of Working Example 3.

| Compound No. | R⁴ |
|---|---|
| 33 | OH |
| 34 | N⏜S (thiomorpholino) |
| 35 | N⏜O (morpholino) |

WORKING EXAMPLE 36

Synthesis of 1-(3,4,5-trimethyl-2,5-benzoquinonyl)-1,2,3,4-tetrahydro-2-naphthaleneacetic acid (Compound No. 36)

To a methylene chloride solution (50 ml) of 1.35 g (7.181 mmole) of the compound of Reference Example 7 (R-7a: R-7b=5:3) and 1.42 g (9.342 mmole) of trimethyl hydroquinone, 250 µl of trifluoromethane sulfonic acid was added and the mixture was stirred at room temperature for 18 hours.

The reaction mixture was washed with water, dried and then concentrated under a reduced pressure. The residue was dissolved in a mixed solution (50 ml) of acetanilide/water (=3/1 (V/V)), and 10.99 g (20.055 mmole) of CAN was added, followed by stirring at room temperature for 30 minutes. The reaction mixture was diluted with water, then extracted with ether, and the extract was washed with water, dried and the solvent was evaporated. The crude product was purified by silica gel chromatography (5% methanol/methylene chloride) to obtain 1.47 g of the title compound.

WORKING EXAMPLES 37–40

The following compounds were prepared from the compound 36 according to a method of Working Example 3.

| Compound No. | R⁴ |
|---|---|
| 36 | OH |
| 37 | N⏜S |
| 38 | N⏜O |
| 39 | N⏜N—Me |
| 40 | OEt |

The physical properties of the compounds obtained above are listed in Table 2.

EVALUATION EXAMPLE 1 (HYPOBARIC HYPOXIA ACTIVITY)

The hypobaric hypoxia activity was determined by using male ddY mice (body weight=22–30 g) as follows.

The test sample was suspended in a 1% gum arabic solution, and orally administered compulsorily at a ratio of 50 mg/kg. The test sample administered group was 7 mice per one group, and the control group (solvent solution administered group) 14 mice. One hour after administration of the test sample, mice were placed in a desiccator, the desiccator was brought to a reduced pressure of 180 mm Hg by a vacuum pump and observation was made for 15 minutes. The time from initiation of the reduction of pressure to a stopping of aspiration was measured as the survival time, and when alive after an elapse of 15 minutes, the survival time was assumed to be 15 minutes.

The ratio of the average survival time of the sample group to that of the control group was as shown in Table 3.

TABLE 3

| Compound No. | Hypobaric Hypoxia Activity Sample (min)/Control (min) |
|---|---|
| 2 | 1.29** |
| 4 | 1.48* |
| 5 | 1.36** |
| 9 | 1.79* |

TABLE 3-continued

| Compound No. | Hypobaric Hypoxia Activity Sample (min)/Control (min) |
|---|---|
| 15a | 1.41 |
| 17a | 1.50** |
| 18a | 1.32 |
| 20 | 1.36* |
| 23 | 1.33* |
| 29 | 1.25* |

TABLE 3-continued

| Compound No. | Hypobaric Hypoxia Activity Sample (min)/Control (min) |
|---|---|
| 30 | 1.18* |
| 33b | 1.46 |
| 35a | 1.48 |

*Significant at a probability level of 5%
**Significant at a probability level of 1%

TABLE 1

| Compound No. | Structure | Property (m.p.) | IR spectrum ($\nu$ cm$^{-1}$) | NMR spectrum ($\delta$ ppm) | Mass spectrum |
|---|---|---|---|---|---|
| R-1 | tetralone-CH₂COOH | Colorless crystalline | 1710, 1682 | 1.85–2.10(1H, m), 2.15–2.35 (1H, m), 2.35–2.60(1H, m), 2.85–3.25(4H, m), 7.15–7.40 (2H, m), 7.48(1H, t), 8.03 (1H, d) | |
| R-2 | tetralone-(CH₂)₂COOH | Colorless crystalline | 1706, 1678 | 1.70–2.05(2H, m), 2.10–2.40 (2H, m), 2.40–2.70(3H, m), 2.90–3.10(2H, m), 7.10–7.40 (2H, m), 7.46(1H, t), 8.01 (1H, d) | |
| R-3 | tetralone-(CH₂)₃COOH | Colorless crystalline 59–61° C. | 1708, 1679 (CHCl₃) | 1.40–2.10(5H, m), 2.10–2.60 (4H, m), 2.85–3.10(2H, m), 7.05–7.55(4H, m), 8.02 (1H, d) | |
| R-4 | tetralone-COOEt | Colorless oily | 1728, 1683 | 1.25(3H, t), 2.70–3.05 (2H, m), 3.05–3.55(3H, m), 4.17(2H, q), 7.20–7.40 (2H, m), 7.50(1H, t), 8.03 (1H, d) | |
| R-5 | chromone-CH₂COOEt | Colorless crystalline 77–78° C. | 1732, 1646 | 1.28(3H, t), 3.48(2H, s), 4.19(2H, q), 7.30–7.55 (2H, m), 7.60–7.75(1H, m), 7.95(1H, s), 8.15–8.30 (1H, m) | |
| R-6 | chromone-(CH₂)₂COOEt | Colorless crystalline 64–65° C. | 1722, 1640 | 1.22(3H, t), 2.55–2.85 (4H, m), 4.12(2H, q), 7.30–7.50(2H, m), 7.55–7.75 (1H, m), 7.90(1H, s), 8.15–8.30(1H, m) | |
| R-7a | lactone-fused tetralin | 134–136° C. | 1782 | 1.65–1.95(1H, m), 2.10–2.55 (3H, m), 2.55–2.85(1H, m), 2.85–3.15(2H, m), 4.97 (1H, d, J=10.4Hz), 7.0–7.5 (4H, m) | |
| R-7b | lactone-fused tetralin | Colorless crystalline 102–103° C. | 1766 | 1.50–1.75(1H, m), 1.80–2.00 (1H, m), 2.30–2.50(1H, m), 2.60–3.00(4H, m), 5.42(1H, d, J=6.1Hz), 7.05–7.55 (4H, m) | |

TABLE 1-continued

| | | | | | |
|---|---|---|---|---|---|
| R-8b | (structure) | Colorless crystalline 85–86° C. | 1770 (CHCl₃) | 1.37(3H, d), 1.65–1.90 (1H, m), 1.90–2.10(1H, m), 2.35–2.60(2H, m), 2.60–2.95 (2H, m), 5.52(1H, d), 7.00–7.55(4H, m) | 202 (M⁺) 129 (100) |
| R-8a | (structure) | Colorless crystalline 110–112° C. | 1778 (CHCl₃) | 1.25(3H, d), 1.70–1.95 (1H, m), 1.95–2.15(1H, m), 2.25–2.45(1H, m), 2.70–2.90 (1H, m), 2.90–3.10(2H, m), 5.13(1H, d), 7.05–7.50 (5H, m) | 202 (M⁺) 91 (100) |
| R-9a | (structure) | 144–146° C. | 1726 | 1.45–1.80(2H, m), 1.80–2.20 (3H, m), 2.55–3.10(4H, m), 5.10(1H, d, J=10.4Hz), 7.00–7.30(3H, m), 7.50–7.70 (1H, m) | |
| R-9b | (structure) | 75–76° C. | 1728 | 1.60–2.00(3H, m), 2.10–2.40 (2H, m), 2.40–2.70(2H, m), 2.70–3.00(2H, m), 5.32(1H, d, J=5.2Hz), 7.00–7.55 (4H, m) | |
| R-10(1) | (structure) isomer mixture | Colorless oily | 1724 1638 (CHCl₃) | 1.20–1.55(2H, m), 1.55–1.90 (4H, m), 1.90–2.20(1H, m), 2.04 and 2.10(3H, each s)- 2.20–2.45(2H, m), 2.50–2.70 (4H, m), 2.70–3.00(2H, m), 3.60–4.00(4H, m), 5.79 and 6.08(1H, d and s-like) 7.00–7.40(4H, m) | 361 (M⁺) 43 (100) |
| R-10(2) | (structure) isomer mixture | Colorless oily | 1728 1636 (CHCl₃) | 1.20–1.55(2H, m), 1.55–1.90 (4H, m), 1.90–2.20(1H, m), 2.04 and 2.10(3H, each s), 2.20–2.40(2H, m), 2.70–3.00 (2H, m), 3.35–3.75(8H, m), 5.78, 6.07(1H, each d) 7.05–7.40(4H, m) | 345 (M⁺) 129 (100) |
| R-10(3) | (structure) isomer mixture | Colorless oily | 1733 1630 (CHCl₃) | 1.20–1.90(9H, m), 1.90–2.20 (1H, m), 2.03 and 2.09 (3H, each s), 2.20–2.40 (2H, m), 2.70–3.00(2H, m), 3.20–3.65(4H, m), 5.79 and 6.08(1H, d and s-like) 7.05–7.40(4H, m) | 343 (M⁺) 84 (100) |
| R-11 | (structure) | Colorless powder (49–50° C.) | 1768 | 2.20(1H, d), 2.60–2.80 (1H, m), 2.90–3.30(3H, m), 5.29(1H, d), 7.00–7.40 (4H, m) | |

TABLE 1-continued

| Compound | Structure | Property (m.p.) | IR | NMR |
|---|---|---|---|---|
| R-12a | 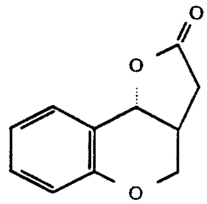 | Colorless powder 118-119° C. | 1788 | 2.35-2.85(3H, m), 4.29 (1H, t), 4.60(1H, d, d), 5.06 (1H, d), 6.70-7.05(2H, m), 7.05-7.35(2H, m) |
| R-12b | 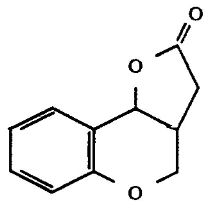 | Colorless powder 101-102° C. | 1770 | 2.44(1H, d, d), 2.86(1H, d, d), 2.90-3.10(1H, m), 3.83 (1H, d, d), 4.21(1H, d, d), 5.49(1H, d), 6.92(1H, d), 7.02(1H, t), 7.15-7.50 (2H, m) |
| R-13a | 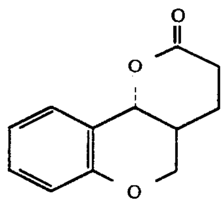 | Colorless powder 139-142° C. | 1738 | 1.50-1.75(1H, m), 1.95-2.40 (2H, m), 2.60-2.95(2H, m), 3.94(1H, t), 4.37(1H, d, d), 5.18(1H, d), 6.84(1H, d), 6.98(1H, t), 7.10-7.35 (1H, m), 7.40(1H, d) |
| R-13b | 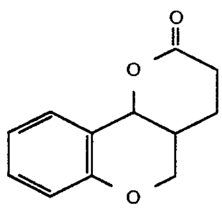 | Colorless powder 106-107° C. | 1740 | 1.45-1.70(1H, m), 2.15-2.40 (1H, m), 2.40-2.75(2H, m), 3.97(1H, t), 4.12(1H, d, d), 5.33(1H, d), 6.87(1H, d), 6.97(1H, t), 7.05-7.45 (2H, m) |
| R-14 | 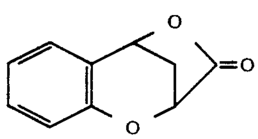 | Oily | 1780 | 2.46(1H, d), 4.50-4.65 (1H, m), 4.80-4.95(1H, m), 5.30-5.40(1H, m), 6.80-7.00 (2H, m), 7.05-7.40(2H, m) |
| R-15a | 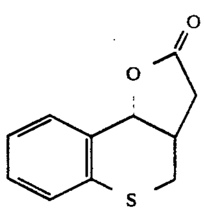 | Colorless crystalline 99-100° C. | 1787 | 2.35-2.65(2H, m), 2.70-2.95 (1H, m), 3.12(1H, t), 3.28 (1H, d, d), 4.94(1H, d, J=9.87Hz), 7.05-7.30(3H, m), 7.42(1H, d) |
| R-15b | 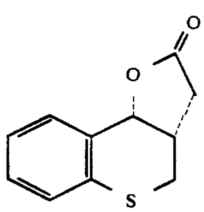 | Colorless crystalline 112-113° C. | 1777 | 2.50-3.05(4H, m), 3.05-3.25 (1H, m), 5.49(1H, d, J=6.6Hz), 7.05-7.35(3H, m), 7.47(1H, d) |

TABLE 2

| Compound No. (Example) | Property (m.p.) | IR spectrum ($\nu$ cm$^{-1}$) | NMR spectrum ($\delta$ ppm) (Temp. 60° C.) | Mass spectrum |
|---|---|---|---|---|
| 1 | Hygroscopic powder | 3000 1704 1647 | 1.50-1.75(1H, m), 1.88 (3H, s), 2.00-2.20(1H, m), 2.20-2.45(2H, m), 2.45-2.70 (1H, m), 2.75-2.95(1H, m), 2.95-3.15(1H, m), 3.94 (3H, s), 4.00(3H, s), | 370 (M$^+$, 100) |

TABLE 2-continued

| Compound No. (Example) | Property (m.p.) | IR spectrum ($\nu$ cm$^{-1}$) | NMR spectrum ($\delta$ ppm) (Temp. 60° C.) | Mass spectrum |
|---|---|---|---|---|
| 2 | Oily | 3000 1708 1648 | 4.15–4.4(1H, m), 6.71 (1H, d), 6.90–7.15(3H, m) 1.30–1.60(2H, m), 1.60–1.90 (1H, m), 1.85(3H, s), 1.90–2.20(2H, m), 2.20–2.65 (2H, m), 2.70–3.10(2H, m), 3.93(3H, s), 4.00(3H, s), 4.10–4.35(1H, m), 6.71 (1H, d), 6.90–7.20(3H, m) | 384 (M$^+$, 100) |
| 3 | 156–157° C. | 1642 | 1.40–1.65(1H, m), 1.98 (3H, s), 2.00–2.15(1H, m), 2.15–2.35(2H, m), 2.40–2.75 (5H, m), 2.75–2.90(1H, m), 2.90–3.15(1H, m), 3.50–3.90 (4H, m), 3.99(3H, s), 4.00 (3H, s), 4.32(1H, d, J = 9.5 Hz), 6.71(1H, d), 6.90–7.15(3H, m) | 455 (M$^+$) 310 (100) |
| 4 | 150–151° C. | 1640 | 1.45–1.65(1H, m), 1.82(3H, s), 2.00–2.15 (1H, m), 2.15–2.30(2H, m), 2.55–2.75(1H, m), 2.75–2.90 (1H, m), 2.90–3.15(1H, m), 3.25–3.70(8H, m), 3.98 (6H, s), 4.33(1H, d, J = 8.7 Hz), 6.70(1H, d), 6.90–7.15(3H, m) | 439 (M$^+$) 310 (100) |
| 5 | Oily | 1643 | 1.40–1.65(1H, m), 1.82 (3H, brs), 2.00–2.15(1H, m), 2.15–2.40(6H, m), 2.27 (3H, s), 2.50–2.75(1H, m), 2.75–2.90(1H, m), 2.90–3.15 (1H, m), 3.25–3.70(4H, m), 3.99(6H, s), 4.20–4.40 (1H, m), 6.70(1H, d), 6.90–7.15(3H, m) | 452 (M$^+$) 98 (100) |
| 6 | Oily | 1642 | 1.30–1.70(7H, m), 1.82 (3H, brs), 2.00–2.15(1H, m), 2.15–2.40(2H, m), 2.50–2.75 (1H, m), 2.75–3.15(2H, m), 3.15–3.60(4H, m), 3.99 (6H, s), 4.20–4.40(1H, m), 6.71(1H, d), 6.90–7.15(3H, m) | 437 (M$^+$) 310 (100) |
| 7 | Oily | 1722 1648 | 1.20(3H, t), 1.50–1.70 (1H, m), 1.88(3H, brs), 2.00–2.15(1H, m), 2.15–2.35 (2H, m), 2.45–2.70(1H, m), 2.70–2.90(1H, m), 2.90–3.15 (1H, m), 3.97(3H, s), 3.99 (3H, s), 4.07(2H, q), 4.15–4.35((1H, m), 6.69 (1H, d), 6.90–7.15(3H, m) | 398 (M$^+$, 100) |
| 8 | Hygroscopic powder | 1642 | 1.30–1.60(2H, m), 1.65–1.95 (1H, m), 1.83(3H, s), 1.95–2.70(8H, m), 2.70–3.10 (2H, m), 3.50–4.00(4H, m), 3.93(3H, s), 4.00(3H, s), 4.10–4.35(1H, m), 6.70 (1H, d), 6.85–7.20(3H, m) | 469 (M$^+$) 310 (100) |
| 9 | 117–118° C. | 1646 | 1.30–1.60(2H, m), 1.65–1.95 (1H, m), 1.87(3H, s), 2.00–2.55(4H, m), 2.75–3.10 (2H, m), 3.30–3.70(8H, m), 3.94(3H, s), 4.01(3H, s), 4.10–4.35(1H, m), 6.73 (1H, d), 6.90–7.15(3H, m) | 453 (M$^+$) 88 (100) |
| 10 | Reddish yellow oily | 1645 1730 | 1.21(3H, t)1.30–1.60(2H, m) 1.85(3H, s)1.60–2.20(3H, m) 2.20–2.50(2H, m)2.75–3.10(2H, m) 3.95(3H, s)4.1(3H, s)4.08(2H, q) 4.00–4.35(1H, br, m)6.71(1H, d) 6.90–7.20(3H, m) | 412 (M$^+$, 100) |
| 11 | Oily | 1648 (CHCl$_3$) | 1.10–1.65(4H, m), 1.65–2.35 (5H, m), 1.83(3H, s), 2.45–2.70(4H, m), 2.70–3.10 (2H, m), 3.60–3.95(4H, m), 3.96(3H, s), 4.01(3H, s), 4.00–4.35(1H, m), 6.69 (1H, d), 6.90–7.15(3H, m), | 483 (Mt$^+$) 184 (100) |

TABLE 2-continued

| Compound No. (Example) | Property (m.p.) | IR spectrum ($\nu$ cm$^{-1}$) | NMR spectrum ($\delta$ ppm) (Temp. 60° C.) | Mass spectrum |
|---|---|---|---|---|
| 12 | Oily | 1644 (CHCl$_3$) | (55° C.) 1.10–1.65(4H, m), 1.65–1.95 (1H, m), 1.83(3H, s), 1.95–2.30(4H, m), 2.75–3.05 (2H, m), 3.30–3.75(8H, m), 3.95(3H, s), 4.01(3H, s), 4.10–4.35(1H, m), 6.68 (1H, d), 6.90–7.15(3H, m) | 467 (Mt$^+$) 184 (100) |
| 13 | Oily | 1645 (CHCl$_3$) | (55° C.) 1.10–2.30(18H, m), 2.70–3.10 (2H, m), 3.25–3.55(4H, m), 3.95(3H, s), 4.01(3H, s), 4.05–4.35(1H, m), 6.68 (1H, d), 6.90–7.15(3H, m) | 465 (Mt$^+$) 127 (100) |
| 14a | Yellow powder (76–78° C.) | 1710 1652 | 1.79(3H, brs), 1.85–2.15 (1H, m), 2.20–2.35(1H, m), 2.75–2.95(1H, m), 3.11 (2H, d), 3.93(3H, s), 4.00 (3H, s), 4.45–4.75(1H, m), 6.77(1H, d), 6.95–7.15 (3H, m), (60° C.*) | |
| 14b | Yellow crystalline (156–159° C.) | 1706 1652 | 1.93(3H, s), 2.00–2.20 (1H, m)2.20–2.40(1H, m), 3.00–3.25(3H, m), 3.91 (3H, s), 4.00(3H, s), 4.45–4.65(1H, m), 6.74 (1H, d), 6.90–7.25(3H, m) | |
| 15a | Yellow powder (87–89° C.) | 1644 | 1.68(3H, brs), 1.85–2.20 (2H, m), 2.50–2.75(4H, m), 2.75–2.90(1H, m), 2.90–3.10 (1H, m), 3.10–3.30(1H, m), 3.70–4.00(4H, m), 3.98 4.55–4.85(1H, m), 6.80 (1H, d), 6.95–7.20(3H, m), (60° C.*) | |
| 15b | Yellow powder (58–60° C.) | 1644 | 1.97(3H, s), 1.85–2.05 (1H, m), 2.15–2.35(1H, m), 2.50–2.70(4H, m), 3.01 (2H, d), 3.15–3.35(1H, m), 3.65–4.00(4H, m), 3.93 (3H, s), 4.02(3H, s), 4.50 (1H, t), 6.77(1H, d), 6.95–7.20(3H, m) | |
| 16a | Yellow powder (80–82° C.) | 1644 | 1.68(3H, s), 1.85–2.15 (2H, m), 2.75–2.90(1H, m), 2.90–3.10(1H, m), 3.10–3.35 (1H, m), 3.45–3.80(8H, m), 3.98(3H, s), 3.99(3H, s), 4.60–4.85(1H, m), 6.80 (1H, d), 6.95–7.20(3H, m), (60° C.*) | |
| 17a | Yellow crystalline (69–71° C.) | 1644 | 1.07(3H, brs), 1.85–2.20 (2H, m), 2.31(3H, s), 2.20–2.60(4H, m), 2.75–2.90 (1H, m), 2.90–3.10(1H, m), 3.10–3.30(1H, m), 3.45–3.75 (4H, m), 3.98(3H, s), 3.99 (3H, s), 4.55–4.90(1H, m), 6.80(1H, d), 6.90–7.20 (3H, m),(60° C.*) | |
| 18a | Oily | 1728 1650 | 1.78(3H, s), 1.80–2.10 (1H, m), 2.15–2.35(1H, m), 2.75–2.95(1H, m), 3.00–3.20 (2H, m), 3.95–(3H, s), 4.00 (3H, s), 4.50–4.75(1H, m), 5.18(2H, s), 6.77(1H, d), 6.95–7.15(3H, m), 7.15–7.45 (5H, m) | |
| 18b | Oily | 1724 1646 | 1.83(3H, s), 2.00–2.20 (1H, m, 2.25–2.45(1H, m), 3.05–3.30(3H, m), 3.93 (3H, s), 4.00(3H, s), 4.40–4.55(1H, m), 5.12 (2H, s), 6.73(1H, d), 6.95–7.40(8H, m) | |
| 19 | Yellow crystalline 137–139° C. | 3000 1708 1647 | 1.81(3H, brs), 2.15–2.40 (2H, m), 2.70–2.95(1H, m), 3.85(1H, t), 3.97(3H, s), 4.00(3H, s), 4.30–4.55 | 372 (M$^+$) |

TABLE 2-continued

| Compound No. (Example) | Property (m.p.) | IR spectrum ($\nu$ cm$^{-1}$) | NMR spectrum ($\delta$ ppm) (Temp. 60° C.) | Mass spectrum |
|---|---|---|---|---|
| 20 | Yellow crystalline 159–161° C. | 3000 1708 1648 | (2H, m), 6.60–6.90(3H, m), 7.08(1H, t), (Temp. 55° C.) 1.35–1.60(1H, m), 1.60–1.90 (4H, m), 2.15–2.55(3H, m), 3.76(1H, t), 3.97(3H, s), 4.01(3H, s), 4.15–4.50 (2H, m), 6.60–6.90(3H, m), 6.95–7.15(1H, m), (Temp. 55° C.) | 386 (M$^+$ 100) |
| 21 | Yellow crystalline 187–189° C. | 1646 | 1.76(3H, s), 2.10–2.35 (2H, m), 2.40–2.65(4H, m), 2.80–3.00(1H, m), 3.55–3.95 (5H, m), 4.02(6H, s), 4.25–4.55(2H, m), 6.65–6.90 (3H, m), 7.08(1H, t), (Temp. 55° C.) | 457 (M$^+$ 100) |
| 22 | Yellow crystalline 186–187° C. | 1644 | 1.70(3H, brs), 2.10–2.35 (2H, m), 2.75–3.00(1H, m), 3.30–3.70(8H, m), 3.82 (1H, t), 4.02(6H, s), 4.40 (1H, d, d), 4.25–4.60(1H, m), 6.65–6.90(3H, m), 7.10 (1H, t) | 441 (M$^+$) 258 (100) |
| 23 | Yellow crystalline 147–149° C. | 1641 | 1.77(3H, brs), 2.27(3H, s), 2.10–2.40(6H, m), 2.80–3.00 (1H, m), 3.25–3.65(4H, m), 3.82(1H, t), 4.00(6H, s), 4.30–4.50(2H, m), 6.65–6.90 (3H, m), 7.00–7.15(1H, m) | 454 (M$^+$ 100) |
| 24 | Yellow powder | 1644 | 1.40–1.65(1H, m), 1.65–1.95 (4H, m), 2.15–2.20(3H, m), 3.50–3.65(4H, m), 3.60–3.90 (5H, m), 3.97(3H, s), 4.01 (3H, s), 4.31(1H, d, d), 4.15–4.45(H, m), 6.65–6.90 (3H, m), 7.06(1H, t), (Temp. 55° C.) | 471 (M$^+$) 440 (100) |
| 25 | Yellow powder | 1646 | 1.30–1.65(1H, m), 1.65–1.95 (4H, m), 2.10–2.50(3H, m), 3.25–3.70(8H, m), 3.79 (1H, t), 3.97(3H, s), 4.01 (3H, s), 4.20–4.45(2H, m), 6.60–6.90(3H, m), 6.95–7.15 (1H, m) | 455 (M$^+$) 424 (100) |
| 26 | Oily | 3000 1728 1650 | 1.86(3H, s), 2.30–2.60 (2H, m), 3.97(3H, s), 4.01 (3H, s), 4.35–4.60(1H, m), 4.90–5.10(1H, m), 6.73 (1H, d), 6.84(1H, t), 6.97 (1H, d), 7.14(1H, t) | |
| 27 | Yellow crystalline (144–146° C.) | 1650 | 2.04(3H, s), 2.10–2.50 (2H, m), 2.50–3.00(4H, m), 3.40–4.00(4H, m), 3.92 (3H, s), 4.01(3H, s), 4.70–4.85(1H, m), 5.00–5.15 (1H, m), 6.70–6.95(3H, m), 7.10(1H, t) | |
| 28 | Orange yellow powder (79–81° C.) | 1649 | 2.03(3H, s), 2.15–2.55 (2H, m), 3.35–3.90(8H, m), 3.93(3H, s), 4.00(3H, s), 4.78(1H, t-like), 5.08 (1H, t-like), 6.65–6.95 (3H, m), 7.09(1H, t) | |
| 29 | Yellow crystalline 67–69° C. | 3000 1704 1646 | 1.82(3H, s), 2.38(2H, d), 2.70–3.10(3H, m), 4.00 (3H, s), 4.02(3H, s), 4.47 (1H, d), 6.72(1H, d), 6.93 (1H, t), 7.04(1H, t), 7.13 (1H, d) | 388 (M$^+$ 100) |
| 30 | Yellow crystalline 188–190° C. | 1647 | 1.78(3H, s), 2.28(1H, d, d), 2.41(1H, d, d), 2.40–2.70 (4H, m), 2.75–3.10(3H, m), 3.55–3.95(4H, m), 4.01 (3H, s), 4.02(3H, s), 4.47 (1H, d), 6.73(1H, d), 6.93 (1H, t), 7.04(1H, t)7.13 (1H, d) | 473 (M$^+$) 328 (100) |
| 31 | Yellow crystalline | 1652 | 1.78(3H, s), 2.28(1H, d, d), 2.41(1H, d, d), 2.75–3.10 | 457 (M$^+$) 328 (100) |

TABLE 2-continued

| Compound No. (Example) | Property (m.p.) | IR spectrum ($\nu$ cm$^{-1}$) | NMR spectrum ($\delta$ ppm) (Temp. 60° C.) | Mass spectrum |
|---|---|---|---|---|
| | 182-183° C. | | (3H, m), 3.25-3.75(8H, m), 4.01(3H, s), 4.02(3H, s), 4.47(1H, d), 6.73(1H, d), 6.93(1H, t), 7.04(1H, t), 7.13(1H, d) | |
| 32 | Yellow crystalline 167-169° C. | 1648 | 1.76(3H, s), 2.30-2.50 (2H, m), 2.68(3H, s), 2.55-3.20(7H, m), 3.60-4.20 (4H, m), 4.02(3H, s), 4.03 (3H, s), 4.47(1H, d), 6.75 (1H, d), 6.96(1H, t), 7.07 (1H, t), 7.15(1H, d) | 470 (M$^+$) 70 (100) |
| 33a | Yellow crystals 154-155° C. | 2943 1703 1650 1607 (KBr) | 1.15(3H, d), 1.55-1.80 (1H, m), 1.97(3H, brs), 1.85-2.10(1H, m), 2.40-2.65 (2H, m), 2.75-3.15(2H, m), 3.91(3H, s), 3.97(3H, s), 4.53(1H, d-like), 6.71 (1H, d), 6.85-7.15(3H, m), (Temp. 55° C.) | 384 (M$^+$) 323 (100) |
| 33b | Yellow crystals 157.5-159° C. | 2930 1694 1657 1649 1609 (KBr) | 1.19(3H, d), 1.45-1.70 (1H, m), 1.85(3H, s), 1.80-2.05(1H, m), 2.20-2.45 (1H, m), 2.55-2.75(1H, m), 2.75-3.10(2H, m), 3.96 (3H, s), 4.00(3H, s), 4.25-4.60(1H, m), 6.70 (1H, d), 6.90-7.15(3H m) (Temp. 55° C.) | 384 (M$^+$) 323 (100) |
| 34a | Yellow crystals 165-166.5° C. | 1650 1632 1613 (KBr) | 1.11(3H, d), 1.74(3H, s) 1.75-2.05(2H, m), 2.30-2.75 (6H, m), 2.75-3.10(2H, m), 3.25-3.85(4H, m), 3.98 (3H, s), 4.03(3H, s), 4.58 (1H, d), 6.90(1H, d), 6.90-7.15(3H, m), (Temp. 55° C.) | 469 (M$^+$) 159 (100) |
| 34b | Yellow crystals 108-109° C. | 1651 1635 (KBr) | 1.13(3H, d), 1.35-1.65(1H, m) 1.88(3H, s), 2.05-2.25 (1H, m), 2.35-2.65(6H, m), 2.75-3.10(2H, m), 3.35-4.10 (4H, m), 3.99(6H, s), 4.20-4.40(1H, m), 6.68 (1H, d), 6.90-7.15(3H, m), (Temp. 55° C.) | 469 (M$^+$) 159 (100) |
| 35a | Yellow crystals 167-168.5° C. | 1650 1632 (KBr) | 1.12(3H, d), 1.78(3H, s), 1.80-2.05(2H, m), 2.30-2.50 (1H, m), 2.55-2.75(1H, m), 2.75-3.10(2H, m), 3.15-3.75 (8H, m), 3.98(3H, s), 4.04 (3H, s), 4.58(1H, d), 6.71 (1H, d), 6.90-7.15(3H, m), (Temp. 55° C.) | 453 (M$^+$) 143 (100) |
| 35b | Yellow crystals 134-136° C. | 1650 1631 (KBr) | 1.13(3H, d), 1.40-1.65 (1H, m), 1.89(3H, s), 2.05-2.25(1H, m), 2.40-2.65 (2H, m), 2.80-3.10(2H, m), 3.15-3.70(8H, m), 3.99 (6H, s), 4.20-4.40(1H, m), 6.69(1H, d), 6.90-7.15 (3H, m), (Temp. 55° C.) | 453 (M$^+$) 143 (100) |
| 36 | Yellowish red hygroscopic powder 63-67° C. | 1645 1710 (CHCl$_3$) | 1.40-2.45(13H, m), 2.45-3.20 (3H, m), 4.10-4.40(1H, br, m), 6.60-6.90(1H, m), 6.90-7.35 (3H, m) | 338 (M$^+$ 100) |
| 37 | Yellowish red powder 147-152° C. | 1645 (KBr) | 1.40-3.20(20H, m), 3.40-9.00 (4H, m), 4.15-4.50(1H, m), 6.60-6.85(1H, m), 6.90-7.20 (3H, m) | 423 (M$^+$) 278 (100) |
| 38 | Yellow crystals 179-182° C. | 1642 (KBr) | 1.35-1.65(1H, m), 1.70-2.35 (12H, m), 2.35-3.20(3H, m), 3.2-3.8(8H, m), 4.2-4.45 (1H, m), 6.60-6.80(1H, m), 6.90-7.20(3H, m) | 407 (M$^+$) 278 (100) |
| 39 | Yellow crystalline (hydrochloride) 147-153° C. | 1642 (CHCl$_3$) | 1.40-2.50(20H, m), 2.50-3.20 (3H, m), 3.20-3.7(4H, m), 4.3-4.7(1H, m), 6.60-7.20 (4H, m) | 420 (M$^+$) 278 (100) |

TABLE 2-continued

| Compound No. (Example) | Property (m.p.) | IR spectrum ($\nu$ cm$^{-1}$) | NMR spectrum ($\delta$ ppm) (Temp. 60° C.) | Mass spectrum |
|---|---|---|---|---|
| 40 | Yellow oily | 1648 1728 (CHCl$_3$) | 1.20(3H, t), 1.50–2.40 (13H, m), 2.45–3.15(3H, m), 4.04(2H, q), 4.05–4.40 (1H, m), 6.60–6.90(1H, m), 6.90–7.20(3H, m) | 366 (M$^+$) 278 (100) |

We claim:

1. A compound having the formula (I):

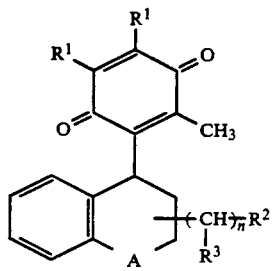

wherein A is —CH$_2$—; R$^1$ is CH$_3$ or OCH$_3$; R$^2$ is a hydroxy, carboxy, carboxylic acid or carboxylic acid ester group; R$^3$ is H or a lower alkyl; and n is 0 or an integer of 1 to 6 and a salt thereof.

2. A compound as claimed in claim 1, wherein R$^2$ is —CO—R$^4$ wherein R$^4$ is a hydroxy group, ethoxy group or benzyloxy group.

3. A compound as claimed in claim 1, represented by the formula (II):

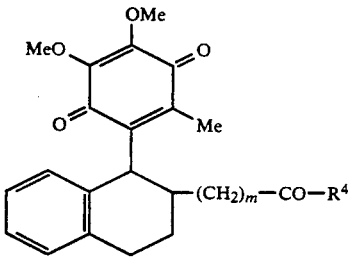

wherein m is 1,2 or 3; R$^4$ is a hydroxy group, ethoxy group or benzyloxy group.

4. A compound as claimed in claim 1, represented by the formula (III):

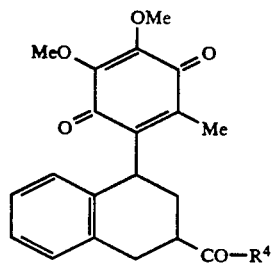

wherein R$^4$ is a hydroxy group, ethoxy group or benzyloxy group.

5. A pharmaceutical composition for treating cerebral insufficiency caused by cerebral ischemia comprising an effective amount of a compound of the formula (I) to improve a cerebral insufficiency caused by cerebral ischemia:

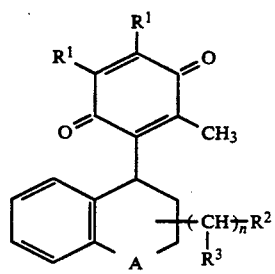

wherein A is —CH$_2$—; R$^1$ is CH$_3$ or OCH$_3$; R$^2$ is a hydroxy, carboxy, carboxylic acid or carboxylic acid ester; R$^3$ is H or a lower alkyl; and n is 0 or an integer of 1 to 6 and a pharmaceutically acceptable carrier therefor.

6. The pharmaceutical composition as claimed in claim 5, represented by the formula (II):

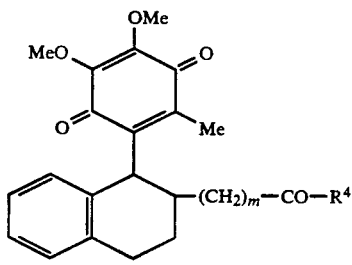

wherein m is 1,2 or 3; R$^4$ is a hydroxy group, ethoxy group or benzyloxy group.

7. The pharmaceutical composition as claimed in claim 5, represented by the formula (III):

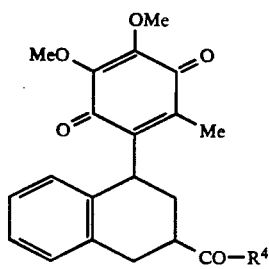

wherein R$^4$ is a hydroxy group, ethoxy group or benzyloxy group.

8. A method for treating cerebral insufficiency caused by cerebral ischemia, comprising administering an effective amount of a compound of the formula (I) to improve cerebral insufficiency caused by cerebral ischemia:

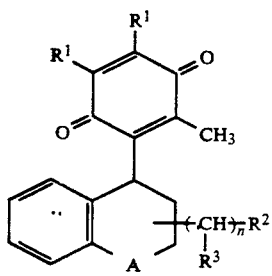

wherein A is —CH$_2$—; R$^1$ is CH$_3$ or OCH$_3$; R$^2$ is a hydroxy, carboxy, carboxylic acid or carboxylic acid ester; R$^3$ is H or a lower alkyl; and n is 0 or an integer of 1 to 6 and a salt thereof, to a patient in need of such treatment.

9. The method as claimed in claim 8 for treating cerebral insufficiency caused by cerebral ischemia comprising administering an effective amount of a compound of the formula (II) to improve cerebral insufficiency caused by cerebral ischemia:

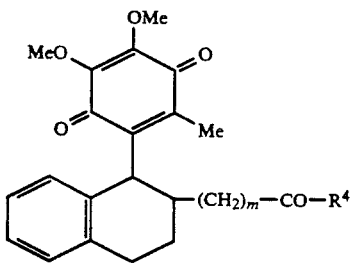

wherein m is 1, 2 or 3; R$^4$ is a hydroxy group, ethoxy group or benzyloxy group.

10. The method as claimed in claim 8 for treating cerebral insufficiency caused by cerebral ischemia comprising administering an effective amount of a compound of the formula (III) to improve cerebral insufficiency caused by cerebral ischemia:

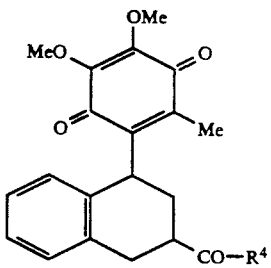

wherein R$^4$ is a hydroxy group, ethoxy group or benzyloxy group, to a patient in need of such treatment.

* * * * *